US012780805B2

(12) United States Patent
Tapinos et al.

(10) Patent No.: US 12,780,805 B2
(45) Date of Patent: Nov. 3, 2026

(54) NITROPHENYL-ACRYLAMIDES AND USES THEREOF

(71) Applicants: BROWN UNIVERSITY, Providence, RI (US); Rhode Island Hospital, Providence, RI (US)

(72) Inventors: Nikolaos Tapinos, Barrington, RI (US); John Zepecki, Johnston, RI (US); David Karambizi, Providence, RI (US)

(73) Assignees: Brown University, Providence, RI (US); Rhode Island Hospital, Providence, RI (US)

( * ) Notice: Subject to any disclaimer, the term of this patent is extended or adjusted under 35 U.S.C. 154(b) by 434 days.

(21) Appl. No.: 18/555,505

(22) PCT Filed: Apr. 15, 2022

(86) PCT No.: PCT/US2022/025068

§ 371 (c)(1),
(2) Date: Oct. 13, 2023

(87) PCT Pub. No.: WO2022/221689

PCT Pub. Date: Oct. 20, 2022

(65) Prior Publication Data

US 2025/0074894 A1 Mar. 6, 2025

Related U.S. Application Data

(60) Provisional application No. 63/175,476, filed on Apr. 15, 2021.

(51) Int. Cl.
*C07D 403/04* (2006.01)
*A61K 31/277* (2006.01)
(Continued)

(52) U.S. Cl.
CPC .......... *C07D 403/04* (2013.01); *A61K 31/277* (2013.01); *A61K 31/341* (2013.01); *A61K 31/397* (2013.01); *A61K 31/4015* (2013.01); *A61K 31/4025* (2013.01); *A61K 31/4155* (2013.01); *A61K 31/4166* (2013.01); *A61K 31/4245* (2013.01); *A61K 31/4402* (2013.01);
(Continued)

(58) Field of Classification Search
CPC ..... C07D 403/04; A61K 31/277; A61P 35/00; C07C 255/23
See application file for complete search history.

(56) References Cited

U.S. PATENT DOCUMENTS

2019/0183842 A1 6/2019 Huang et al.

FOREIGN PATENT DOCUMENTS

WO 2009084031 7/2009
WO 2016206573 A1 12/2016
(Continued)

OTHER PUBLICATIONS

Stupp et al., "Radiotherapy plus Concomitant and Adjuvant Temozolomide for Glioblastoma", N Engl J Med 352, pp. 987-996 (2005).
(Continued)

*Primary Examiner* — San Ming R Hui
(74) *Attorney, Agent, or Firm* — Pabst Patent Group LLP

(57) ABSTRACT

Provided herein are nitrophenyl-acrylamide compounds, their preparation, and uses thereof.

21 Claims, 14 Drawing Sheets

(51) Int. Cl.

| | |
|---|---|
| ***A61K 31/341*** | (2006.01) |
| ***A61K 31/397*** | (2006.01) |
| ***A61K 31/4015*** | (2006.01) |
| ***A61K 31/4025*** | (2006.01) |
| ***A61K 31/4155*** | (2006.01) |
| ***A61K 31/4166*** | (2006.01) |
| ***A61K 31/4245*** | (2006.01) |
| ***A61K 31/4402*** | (2006.01) |
| ***A61K 31/505*** | (2006.01) |
| ***A61P 35/00*** | (2006.01) |
| ***C07C 255/23*** | (2006.01) |
| ***C07C 323/25*** | (2006.01) |
| ***C07D 205/04*** | (2006.01) |
| ***C07D 207/09*** | (2006.01) |
| ***C07D 207/27*** | (2006.01) |
| ***C07D 207/273*** | (2006.01) |
| ***C07D 213/30*** | (2006.01) |
| ***C07D 233/40*** | (2006.01) |
| ***C07D 233/64*** | (2006.01) |
| ***C07D 239/26*** | (2006.01) |
| ***C07D 295/125*** | (2006.01) |
| ***C07D 307/22*** | (2006.01) |
| ***C07D 405/04*** | (2006.01) |
| ***C07D 413/04*** | (2006.01) |

(52) U.S. Cl.

CPC ............ *A61K 31/505* (2013.01); *A61P 35/00* (2018.01); *C07C 255/23* (2013.01); *C07C 323/25* (2013.01); *C07D 205/04* (2013.01); *C07D 207/09* (2013.01); *C07D 207/27* (2013.01); *C07D 207/273* (2013.01); *C07D 213/30* (2013.01); *C07D 233/40* (2013.01); *C07D 233/64* (2013.01); *C07D 239/26* (2013.01); *C07D 295/125* (2013.01); *C07D 307/22* (2013.01); *C07D 405/04* (2013.01); *C07D 413/04* (2013.01)

(56) References Cited

FOREIGN PATENT DOCUMENTS

| | | | | | |
|---|---|---|---|---|---|
| WO | WO-2018049000 | A1 * | 3/2018 | ........... | A61K 31/711 |
| WO | 2022/221689 | A1 | 10/2022 | | |

OTHER PUBLICATIONS

Stupp et al., “The role of radio- and chemotherapy in glioblastoma”, Onkologie 28, pp. 315-317 (2005).

Singh et al., “Identification of a Cancer Stem Cell in Human Brain Tumors”, Cancer Res 63, pp. 5821-5828 (2003).

Singh et al., “Identification of human brain tumour initiating cells”, Nature 432, pp. 396-401 (2004).

Lee et al., “Tumor stem cells derived from glioblastomas cultured in bFGF and EGF more closely mirror the phenotype and genotype of primary tumors than do serum-cultured cell lines”, Cancer Cell 9, pp. 391-403 (2006).

Soni et al., “CD24 and Nanog expression in Stem Cells in Glioblastoma: Correlation with Response to Chemoradiation and Overall Survival”, Asian Pac J Cancer Prev 18, pp. 2215-2219 (2017).

Ben-Porath et al., “An embryonic stem cell-like gene expression signature in poorly differentiated aggressive human tumors”, Nature genetics 40, pp. 499-507 (2008).

Jin et al., “Targeting Glioma Stem Cells through Combined BMI1 and EZH2 Inhibition”, Nat Med 23, pp. 1352-1361 (2017).

Huff, Sarah, et al. “m6A-RNA demethylase FTO inhibitors impair self-renewal in glioblastoma stem cells.” ACS chemical biology 16.2 (2021): 324-333.

Peng, Shiming, et al. “Identification of entacapone as a chemical inhibitor of FTO mediating metabolic regulation through FOXO1.” Science Translational Medicine 11.488 (2019): eaau7116.

International Search Report and Written Opinion, dated Jul. 14, 2022, for International Application PCT/US2022/025068.

Cordova et al. “Piggyback drug development: (Molecular docking of Entacapone analogues as direct M. tuberculosis InhA inhibitors)”, Journal of Chemical and Pharaceutical Research, 2015, (7(5): pp. 636-642, especially: p. 638, Table 1, formula 2.

PubChem-SID-329794863, Modify Date: Mar. 14, 2018 (Mar. 14, 2018). p. 2, figure.

Lan, Ning, et al. “FTO—a common genetic basis for obesity and cancer.” Frontiers in genetics 11 (2020): 559138.

* cited by examiner 1-1

1-2

1-3

CORE compound 1

20-1 + 20-2 → 20-3 → 20-4 → 20-5 → 20-6 → 20-7 → Compound 20

29-1

29-2

29-3

29-4

CORE 29-5

29-6

Compound 29

33-1
33-2
33-3
33-4
33-5
Compound 33

35-1
35-2
35-3
35-4
CORE
35-5
Compound 35

DMSO

Compound 31 (70 μM)

NITROPHENYL-ACRYLAMIDES AND USES THEREOF

RELATED APPLICATIONS

This application claims priority of U.S. Provisional Patent Application No. 63/175,476, filed Apr. 15, 2021, the entire contents of which are incorporated herein by reference.

BACKGROUND

Glioblastoma is the most prevalent primary brain tumor, and one of the most lethal cancers due to the presence of tumor-propagating glioma stem cells. Current therapeutic options include surgical resection, chemotherapy, and radiation. Yet these treatments, although perhaps temporarily effective, generally only delay an onset of further symptoms or recurrence and include undesirable side effects. Furthermore, notwithstanding the utility of current therapies, recurrence after therapeutic intervention using these current options is unfortunately inevitable. Thus, additional treatment options are needed.

Accordingly, provided herein are compounds useful for treating a disease, such as a brain tumor, including glioblastoma.

SUMMARY

In some embodiments, provided herein are nitrophenyl-acrylamide compounds, having the following formula:

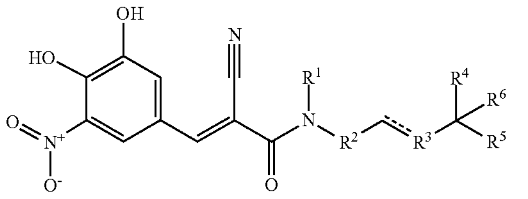

or a pharmaceutically acceptable salt thereof.

In some embodiments, provided herein are nitrophenyl-acrylamide compounds, having the following formula:

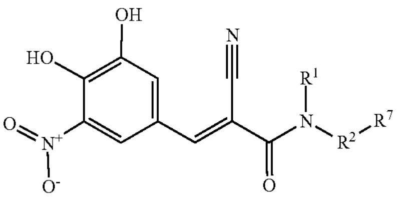

or a pharmaceutically acceptable salt thereof.

In some embodiments, provided herein are methods of

DETAILED DESCRIPTION

Figure 1:
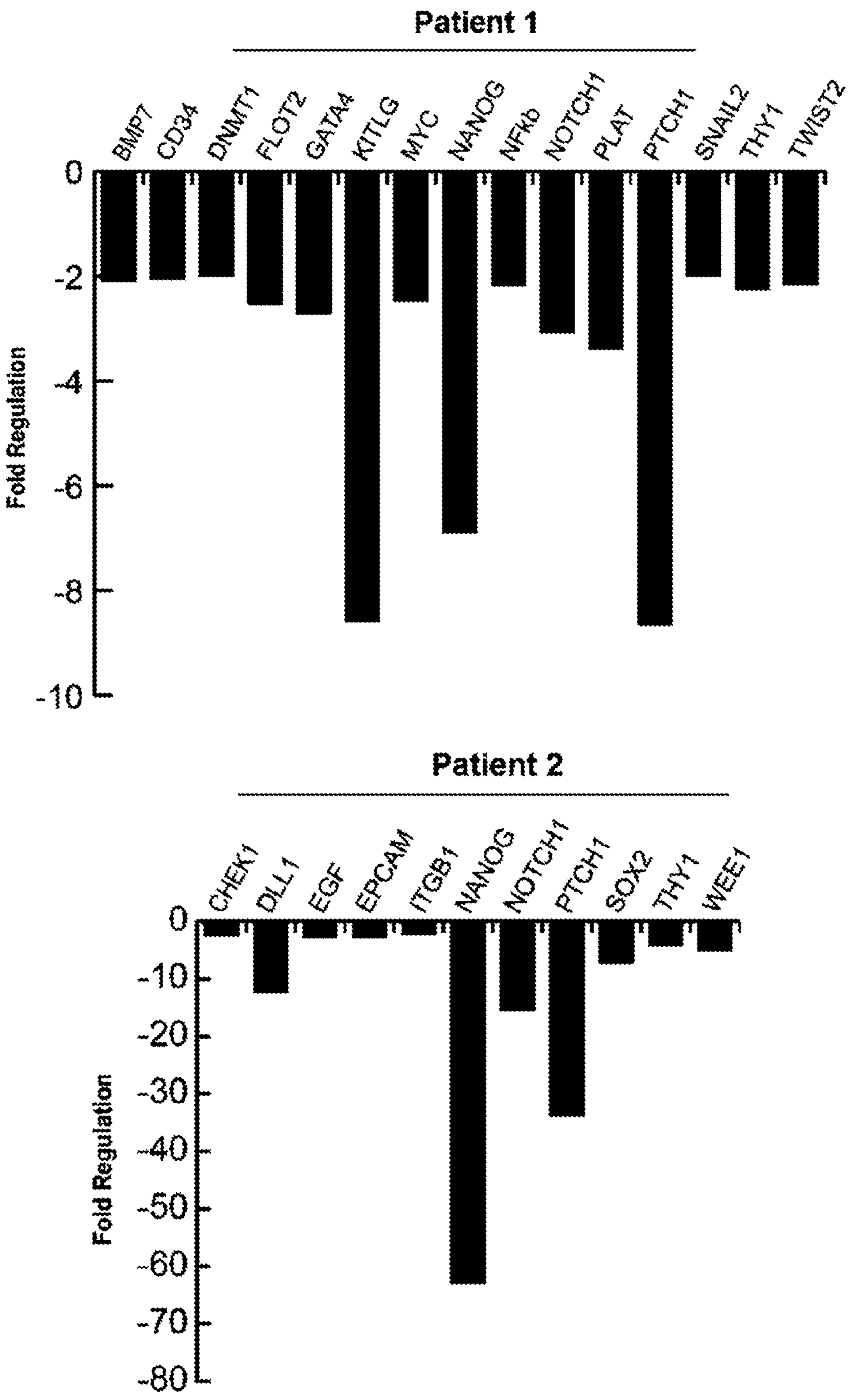
FIG. 1 shows results of a qPCR array in two patient-derived glioma stem cells (GSCs) treated with entacapone for 48 hours. The results show significant inhibition of various cancer stem cell transcripts.

It has been discovered that the nitrophenyl-acrylamide compounds described herein are useful and effective therapeutics, including in treatment of brain tumors, for example glioblastoma. This is surprising because according to the World Health Organization, acrylamide is toxic. Furthermore, acrylamide is not suitable as a cancer therapeutic, but rather is a potentially cancer-causing chemical. Additionally, it has been shown that a derivative of acrylamide, N-(4-nitrophenyl) acrylamide, has low in vitro toxicity on cancer cells with an $IC_{50}$ of 1 mM in Hela cells (Russian Journal of Physical Chemistry B, 2019, 13, 49-61). Accordingly, acrylamides, and nitrophenyl-acrylamides by extension, represent a class of compounds that are potentially cancer-causing and generally understood as ineffective cancer inhibitors.

It has also been discovered that the compounds provided herein are fat mass and obesity-associated protein (FTO) inhibitors. This is useful because overexpression of METTL3 or inhibition of the RNA demethylase FTO suppresses glioma stem cell (GSC) growth and self-renewal. Moreover, inhibition of FTO with the ethyl ester of meclofenamic acid was shown to suppress tumor progression, and substantially prolong lifespan of GSC-grafted mice. Thus, the compounds described herein are useful as FTO inhibitors, or in treating FTO-related disease.

It has also been discovered that the compounds provided herein are Notch1 inhibitors. This is useful because Notch1, a member of the Notch family, is implicated in many types of cancer, including breast cancer (in some embodiments, triple-negative breast cancer), leukemias, brain tumors, lung cancer (in some embodiments, non-small cell lung cancer), and many others. Thus, the compounds described herein are useful as Notch1 inhibitors, or in treating Notch1-related disease.

Compounds/Compositions

Thus, provided herein are nitrophenyl-acrylamides and uses thereof. In some embodiments, provided herein are compounds having the following formula:

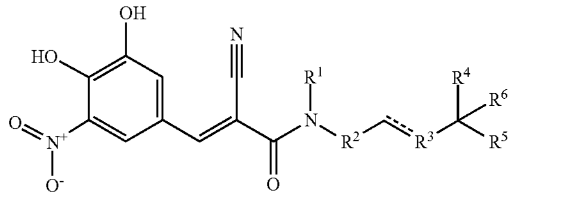

or a pharmaceutically acceptable salt thereof, wherein

 is a single or double bond;

$R^1$ is $C_{1-4}$ alkyl;

$R^2$ is $C_{1-4}$ alkylene;

$R^3$ is N, O, S, NH, CH, or N—($C_{1-4}$ alkyl);

$R^4$ is H, $C_{1-4}$ alkyl, or ($C_{1-4}$ alkyl)-OH;

or $R^3$ and $R^4$ combine to form a $C_{2-6}$ heterocycloalkyl;

$R^5$ is C(O)N(H)($C_{1-4}$ alkyl), C(O)N(H)($C_{2-6}$ heterocycloalkyl), heteroaryl, heteroaryl-($C_{1-4}$ alkyl), C(O)H, CN, pyrrolidinonyl, $C_{1-4}$ alkyl, $C_{1-4}$ haloalkyl, C(O)O($C_{1-4}$ alkyl), C(O)$NH_2$, C(O)N(H)C(O)H, ($C_{1-4}$ alkyl)-OH, $C_{2-6}$ heterocycloalkyl-C(O)H, or O—($C_{1-4}$ alkyl);

or $R^4$ and $R^5$ combine to form CO, $C_{3-7}$ cycloalkyl, $C_{2-6}$ heterocycloalkyl, pyrrolidinonyl, pyrrolidinonyl-($C_{1-4}$ alkyl), or imidazolidinonyl-OH; and $R^6$ is H, CN, C(O)H, $C_{1-4}$ alkyl, heteroaryl, O—($C_{1-4}$ alkyl), O—($C_{1-4}$ alkyl)-OH, N(H)—($C_{1-4}$ alkyl), or N(H)—($C_{1-4}$ alkyl)-OH.

In some embodiments, of the formulae provided herein:

$R^4$ is H, $C_{1-4}$ alkyl, or ($C_{1-4}$ alkyl)-OH;

or $R^3$ and $R^4$ combine to form a $C_{2-6}$ heterocycloalkyl;

$R^5$ is C(O)N(H) ($C_{1-4}$ alkyl), heteroaryl, heteroaryl-($C_{1-4}$ alkyl), C(O)H, CN, pyrrolidinonyl, $C_{1-4}$ alkyl, $C_{1-4}$ haloalkyl, C(O)O($C_{1-4}$ alkyl), C(O)$NH_2$, C(O)N(H) C(O)H, ($C_{1-4}$ alkyl)-OH, or O—($C_{1-4}$ alkyl); and or $R^4$ and $R^5$ combine to form CO, $C_{3-7}$ cycloalkyl, pyrrolidinonyl, pyrrolidinonyl-($C_{1-4}$ alkyl), or imidazolidinonyl-OH.

In some embodiments, provided herein are compounds having the following formula:

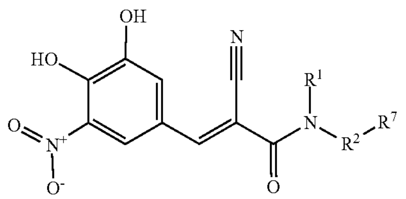

or a pharmaceutically acceptable salt thereof, wherein $R^1$ is $C_{1-4}$ alkyl;

$R^2$ is $C_{1-4}$ alkylene; and $R^7$ is

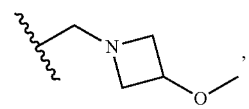, 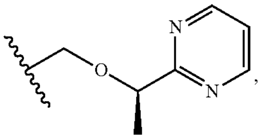,

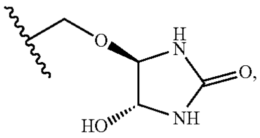 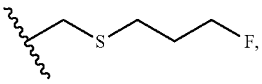

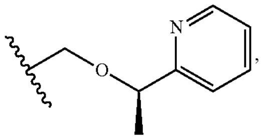,

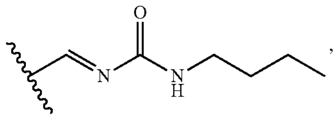, 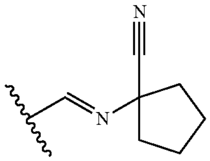,

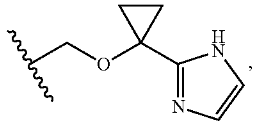, 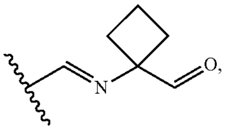

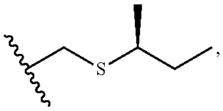, 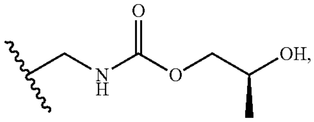

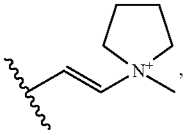, 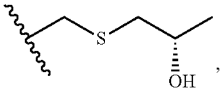,

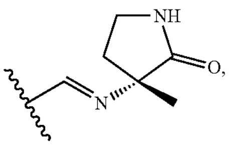 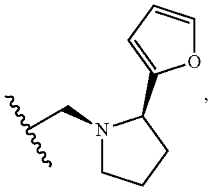,

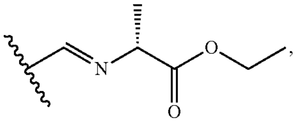, 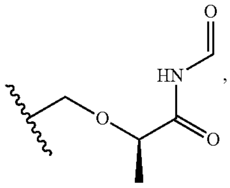,

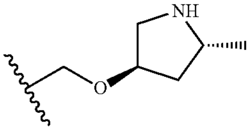, 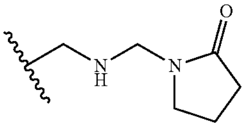,

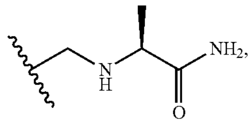 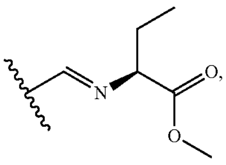

-continued

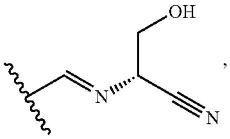
,
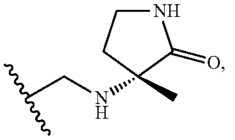

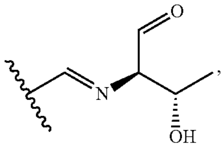
,
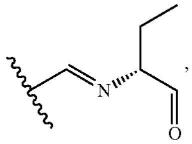
,

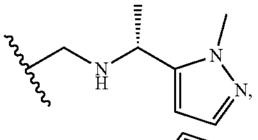

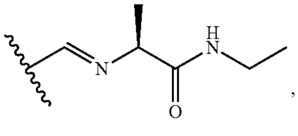
,

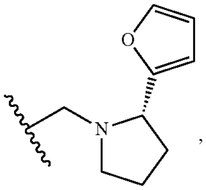
,
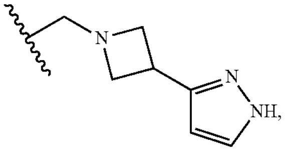

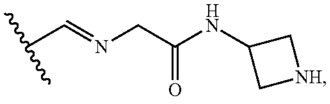

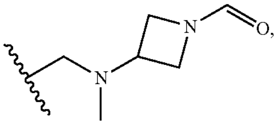

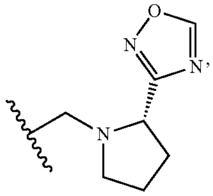
or

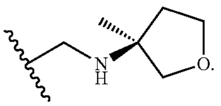

In some embodiments of the formulae provided herein, $R^1$ is methyl or ethyl.

In some embodiments of the formulae provided herein, $R^2$ is methylene.

In some embodiments of the formulae provided herein:

$R^3$ is N, O, S, NH, CH, or N—($C_{1-4}$ alkyl);

$R^4$ is H, $C_{1-4}$ alkyl, or ($C_{1-4}$ alkyl)-OH; and $R^5$ is C(O)N(H) ($C_{1-4}$ alkyl), heteroaryl, heteroaryl-($C_{1-4}$ alkyl), C(O)H, CN, pyrrolidinonyl, $C_{1-4}$ alkyl, $C_{1-4}$ haloalkyl, C(O)O($C_{1-4}$ alkyl), $C(O)NH_2$, C(O)N(H) C(O)H, ($C_{1-4}$ alkyl)-OH, or O—($C_{1-4}$ alkyl).

In some embodiments of the formulae provided herein, $R^3$ is N, NH, or O. In some embodiments, $R^3$ is O or S.

In some embodiments, ⋱ is a single bond, and $R^3$ is N, O, or S.

In some embodiments, ⋱ is a double bond, and $R^3$ is NH or CH.

In some embodiments, $R^4$ is H or $C_{1-4}$ alkyl. In some embodiments, $R^4$ is H, methyl, or ethyl.

In some embodiments, $R^3$ and $R^4$ combine to form a $C_{2-6}$ heterocycloalkyl. In some embodiments, $R^3$ and $R^4$ combine to form a $C_{2-6}$ heterocycloalkyl having one, two or three heteroatoms independently selected from N, O, or S. In some embodiments, $R^3$ and $R^4$ combine to form a $C_{2-5}$ heterocycloalkyl having one or two heteroatoms independently selected from N or O.

In some embodiments, $R^4$ and $R^5$ combine to form CO, $C_{3-7}$ cycloalkyl, pyrrolidinonyl, pyrrolidinonyl-($C_{1-4}$ alkyl), or imidazolidinonyl-OH. In some embodiments, $R^4$ and $R^5$ combine to form CO, $C_{3-4}$ cycloalkyl, pyrrolidinonyl, pyrrolidinonyl-($C_{1-2}$ alkyl), or imidazolidinonyl-OH.

In some embodiments, $R^7$ is

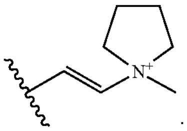 [SMILES: */C=C/[N+]1(C)CCCC1]
.

In some embodiments, $R^7$ is

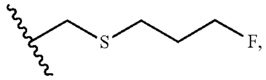

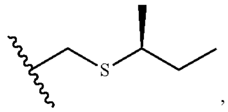
, or

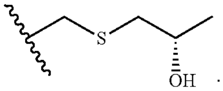
.

In some embodiments, $R^7$ is

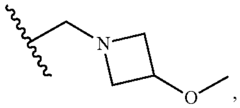
,
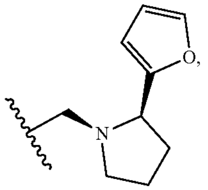

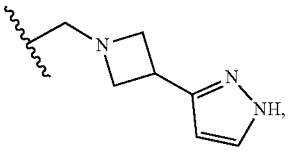
or

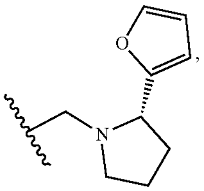
,

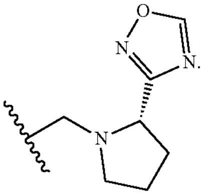

In some embodiments, $R^7$ is

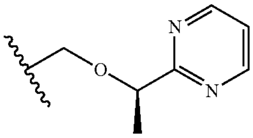,
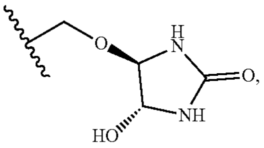
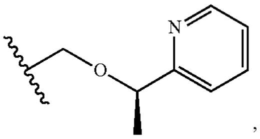,
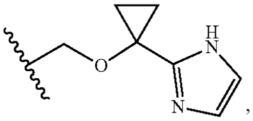,
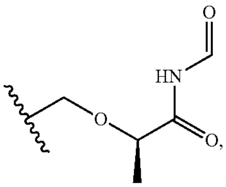 or
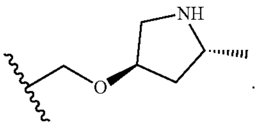.

In some embodiments, $R^7$ is

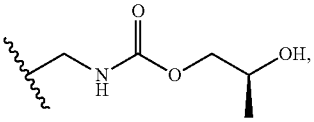
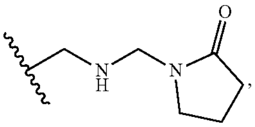,
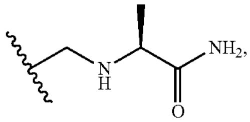
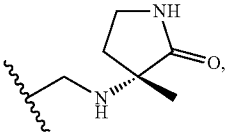 or
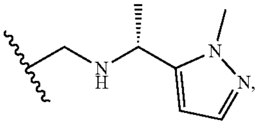
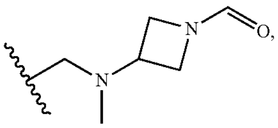 or
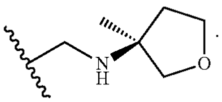.

In some embodiments, $R^7$ is

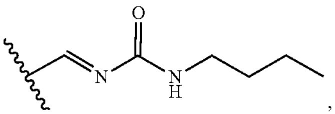,
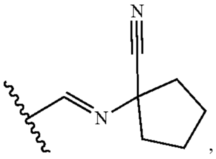,
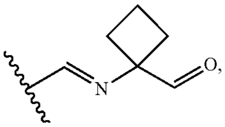
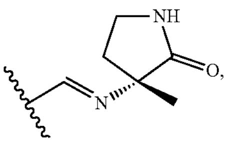
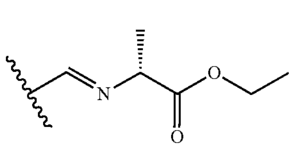,
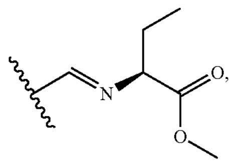
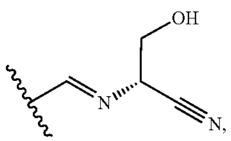
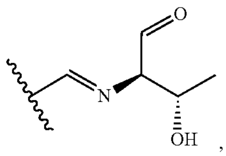,
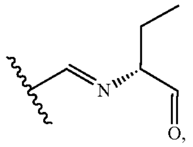
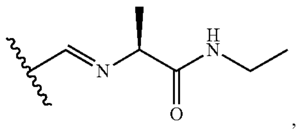, or
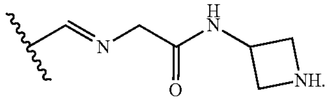

In some embodiments, $R^1$ is ethyl, and $R^2$ is methylene.

In some embodiments of the formulae provided herein, $C_{1-4}$ alkyl refers to methyl, ethyl, propyl, isopropyl, cyclopropyl, butyl, isobutyl, or cyclobutyl.

In some embodiments, the compound provided herein is a compound selected from Table 1, or a pharmaceutically acceptable salt thereof.

TABLE 1

| Compound # | Structure |
| --- | --- |
| 1 | 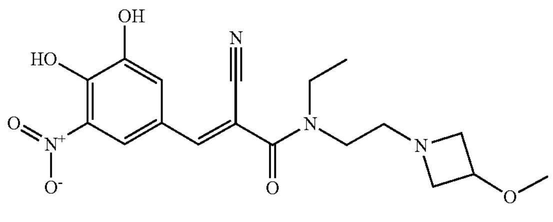 [SMILES: CCN(CCN1CC(OC)C1)C(=O)/C(C#N)=C/c1cc(O)c(O)c([N+](=O)[O-])c1] |

TABLE 1-continued
| Compound # | Structure |
| --- | --- |
| 2 | 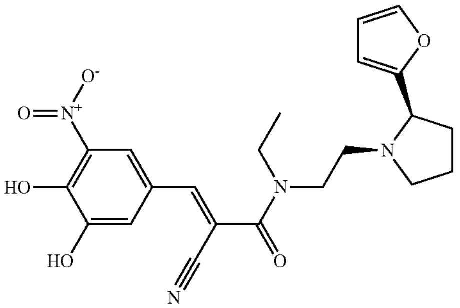 |
| 3 | 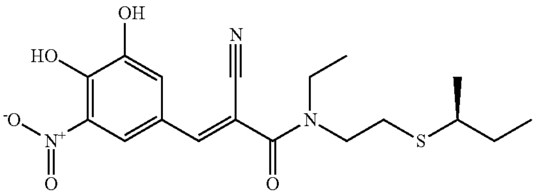 |
| 4 | 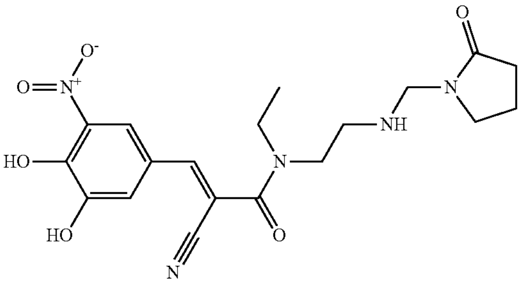 [SMILES: CCN(CCNCN1CCCC1=O)C(=O)/C(C#N)=C/c1cc(O)c(O)c([N+](=O)[O-])c1] |
| 5 | 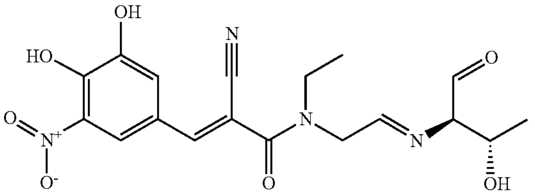 [SMILES: CCN(C/C=N/[C@@H](C=O)[C@H](C)O)C(=O)/C(C#N)=C/c1cc(O)c(O)c([N+](=O)[O-])c1] |
| 6 | 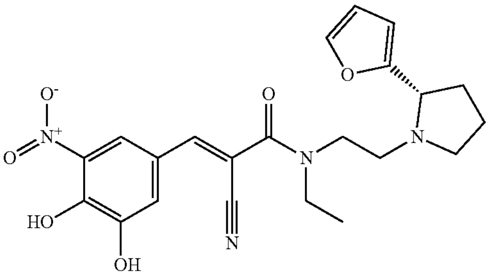 [SMILES: CCN(CCN1CCC[C@H]1c1ccco1)C(=O)/C(C#N)=C/c1cc(O)c(O)c([N+](=O)[O-])c1] |
| 7 | 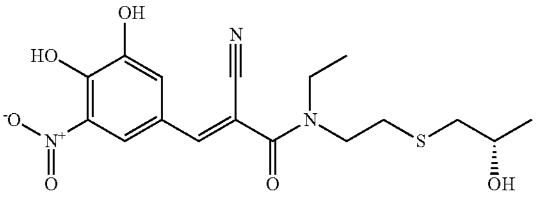 |

TABLE 1-continued
| Compound # | Structure |
| --- | --- |
| 8 | 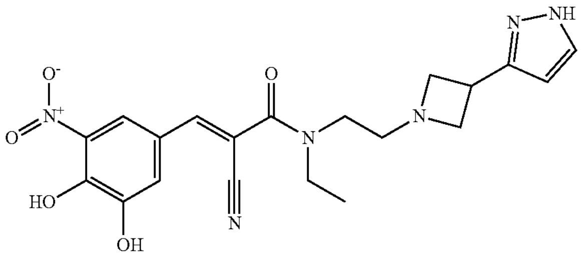 [SMILES: CCN(CCN1CC(c2cc[nH]n2)C1)C(=O)/C(C#N)=C/c1cc(O)c(O)c([N+](=O)[O-])c1] |
| 9 | 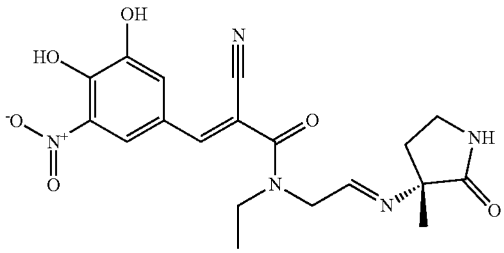 |
| 10 | 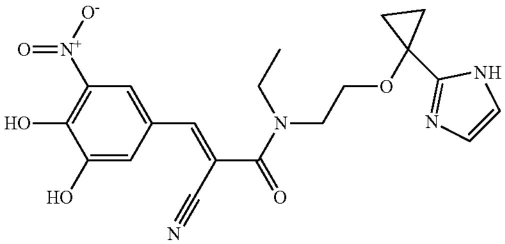 [SMILES: CCN(CCOC1(c2ncc[nH]2)CC1)C(=O)/C(C#N)=C/c1cc(O)c(O)c([N+](=O)[O-])c1] |
| 11 | 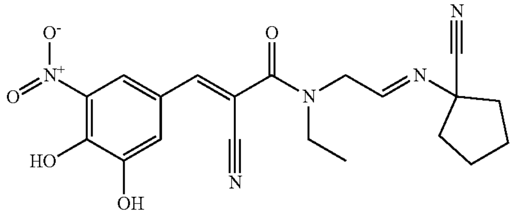 [SMILES: CCN(C/C=N/C1(C#N)CCCC1)C(=O)/C(C#N)=C/c1cc(O)c(O)c([N+](=O)[O-])c1] |
| 12 | 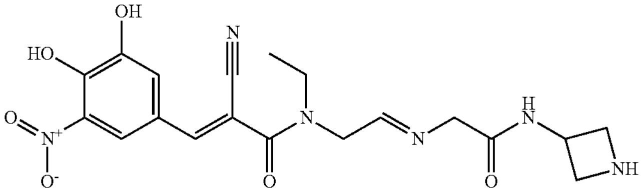 [SMILES: CCN(C/C=N/CC(=O)NC1CNC1)C(=O)/C(C#N)=C/c1cc(O)c(O)c([N+](=O)[O-])c1] |
| 13 | 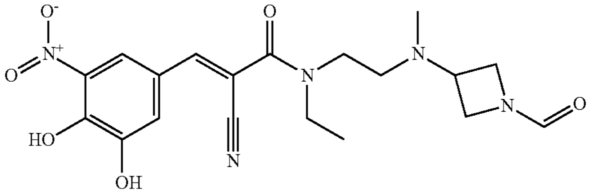 [SMILES: CCN(CCN(C)C1CN(C=O)C1)C(=O)/C(C#N)=C/c1cc(O)c(O)c([N+](=O)[O-])c1] |
| 14 | 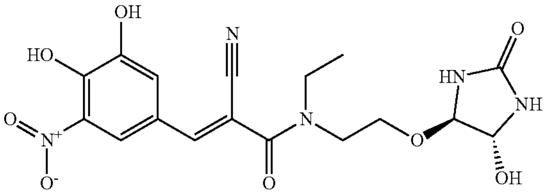 [SMILES: CCN(CCO[C@H]1NC(=O)N[C@@H]1O)C(=O)/C(C#N)=C/c1cc(O)c(O)c([N+](=O)[O-])c1] |

TABLE 1-continued
| Compound # | Structure |
|---|---|
| 15 | 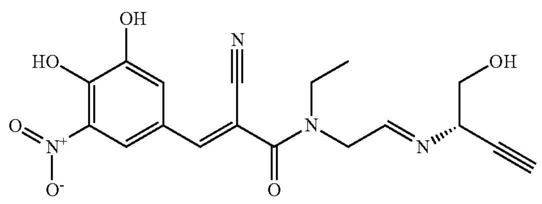 [SMILES: C#C[C@@H](CO)/N=C/CN(CC)C(=O)/C(C#N)=C/c1cc(O)c(O)c([N+](=O)[O-])c1] |
| 16 | 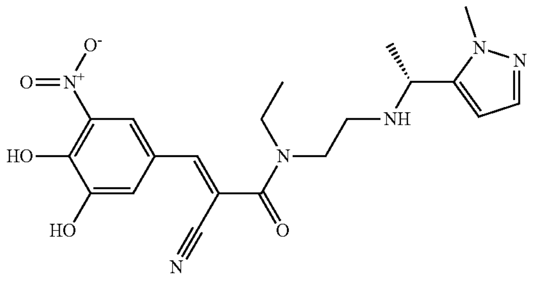 [SMILES: CCN(CCN[C@H](C)c1ccnn1C)C(=O)/C(C#N)=C/c1cc(O)c(O)c([N+](=O)[O-])c1] |
| 17 | 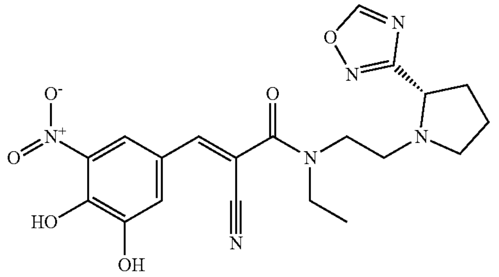 [SMILES: CCN(CCN1CCC[C@H]1c1ncon1)C(=O)/C(C#N)=C/c1cc(O)c(O)c([N+](=O)[O-])c1] |
| 18 | 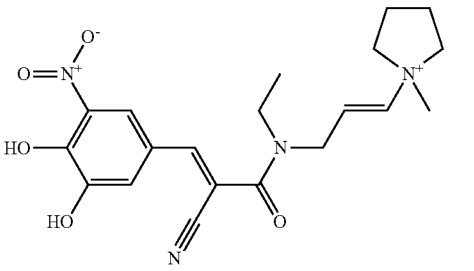 [SMILES: CCN(C/C=C/[N+]1(C)CCCC1)C(=O)/C(C#N)=C/c1cc(O)c(O)c([N+](=O)[O-])c1] |
| 19 | 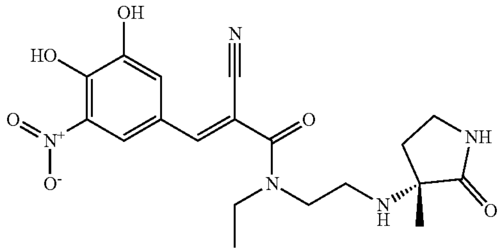 [SMILES: CCN(CCN[C@]1(C)CCNC1=O)C(=O)/C(C#N)=C/c1cc(O)c(O)c([N+](=O)[O-])c1] |
| 20 | 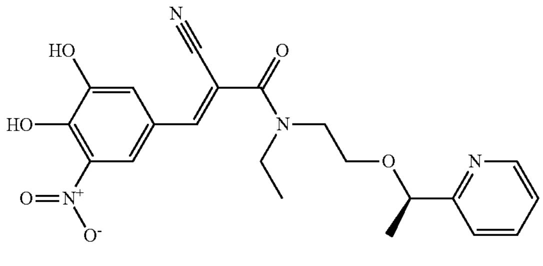 [SMILES: CCN(CCO[C@H](C)c1ccccn1)C(=O)/C(C#N)=C/c1cc(O)c(O)c([N+](=O)[O-])c1] |

TABLE 1-continued
| Compound # | Structure |
| --- | --- |
| 21 | 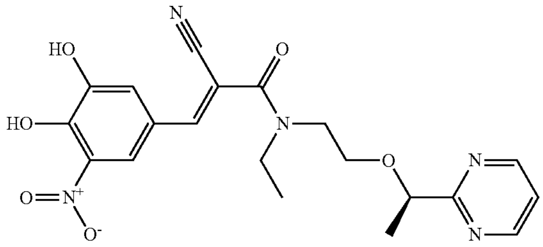 [SMILES: CCN(CCO[C@H](C)c1ncccn1)C(=O)/C(C#N)=C/c1cc(O)c(O)c([N+](=O)[O-])c1] |
| 22 | 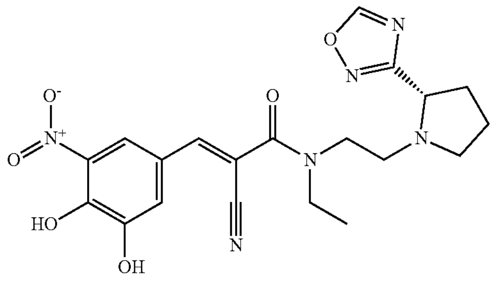 [SMILES: CCN(CCN1CCC[C@H]1c1ncon1)C(=O)/C(C#N)=C/c1cc(O)c(O)c([N+](=O)[O-])c1] |
| 23 | 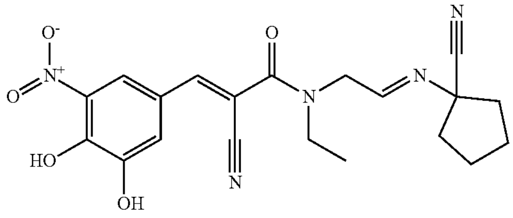 [SMILES: CCN(C/C=N/C1(C#N)CCCC1)C(=O)/C(C#N)=C/c1cc(O)c(O)c([N+](=O)[O-])c1] |
| 24 | 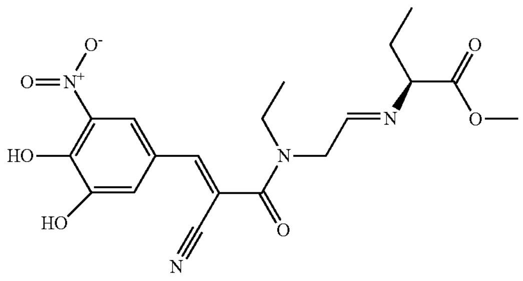 [SMILES: CC[C@H](/N=C/CN(CC)C(=O)/C(C#N)=C/c1cc(O)c(O)c([N+](=O)[O-])c1)C(=O)OC] |
| 25 | 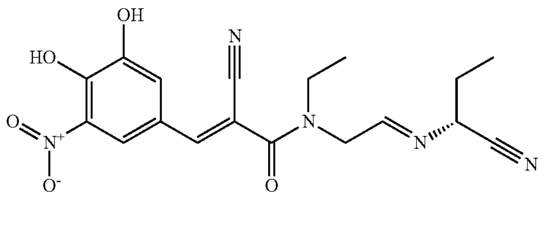 [SMILES: CC[C@H](C#N)/N=C/CN(CC)C(=O)/C(C#N)=C/c1cc(O)c(O)c([N+](=O)[O-])c1] |
| 26 | 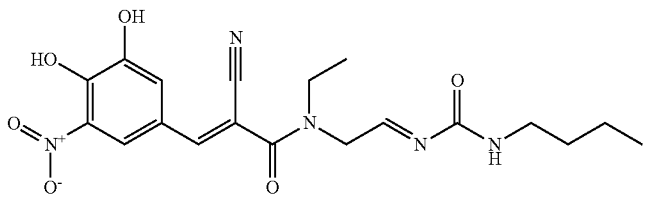 [SMILES: CCCCNC(=O)/N=C/CN(CC)C(=O)/C(C#N)=C/c1cc(O)c(O)c([N+](=O)[O-])c1] |

TABLE 1-continued
| Compound # | Structure |
| --- | --- |
| 27 | 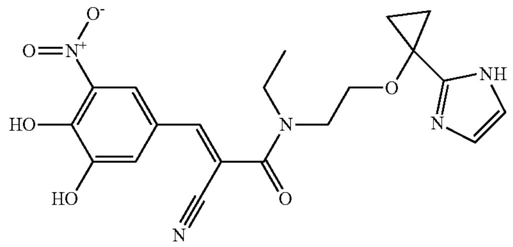 [SMILES: CCN(CCOC1(c2ncc[nH]2)CC1)C(=O)/C(C#N)=C/c1cc(O)c(O)c([N+](=O)[O-])c1] |
| 28 | 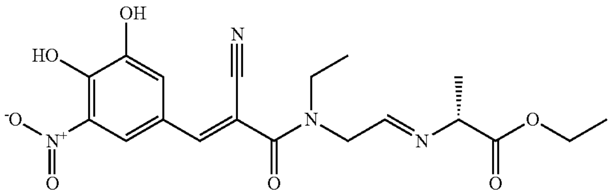 |
| 29 | 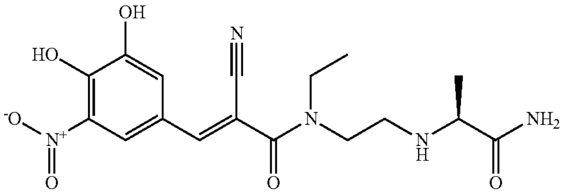 |
| 30 | 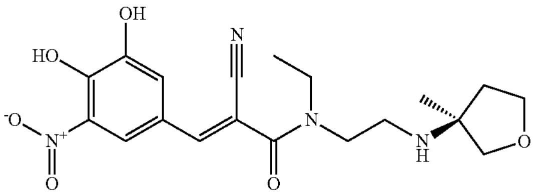 |
| 31 | 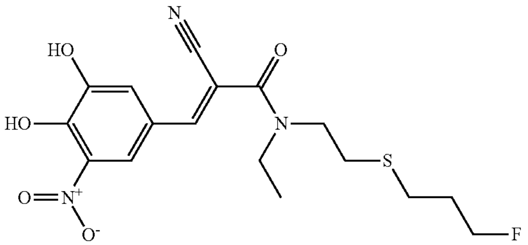 [SMILES: CCN(CCSCCCF)C(=O)/C(C#N)=C/c1cc(O)c(O)c([N+](=O)[O-])c1] |
| 32 | 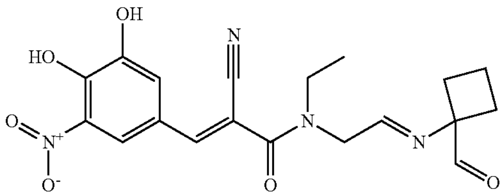 [SMILES: CCN(C/C=N/C1(C=O)CCC1)C(=O)/C(C#N)=C/c1cc(O)c(O)c([N+](=O)[O-])c1] |
| 33 | 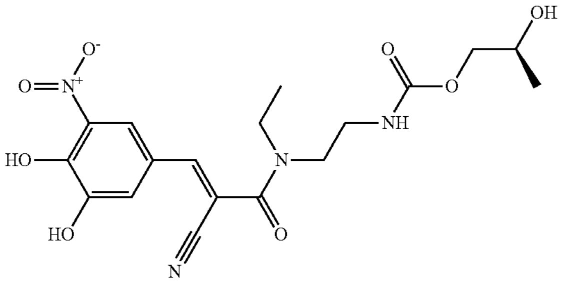 [SMILES: CCN(CCNC(=O)OC[C@H](C)O)C(=O)/C(C#N)=C/c1cc(O)c(O)c([N+](=O)[O-])c1] |

TABLE 1-continued

| Compound # | Structure |
| --- | --- |
| 34 | 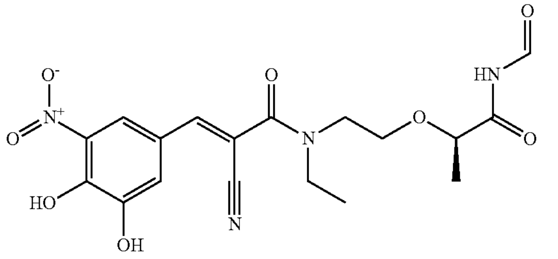 [SMILES: CCN(CCO[C@H](C)C(=O)NC=O)C(=O)/C(C#N)=C/c1cc(O)c(O)c([N+](=O)[O-])c1] |
| 35 | 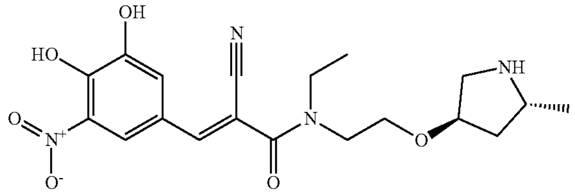 [SMILES: CCN(CCO[C@H]1CN[C@H](C)C1)C(=O)/C(C#N)=C/c1cc(O)c(O)c([N+](=O)[O-])c1] |
| 36 | 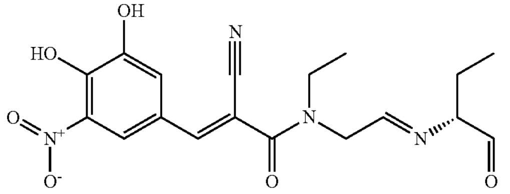 [SMILES: CC[C@H](C=O)/N=C/CN(CC)C(=O)/C(C#N)=C/c1cc(O)c(O)c([N+](=O)[O-])c1] |
| 37 | 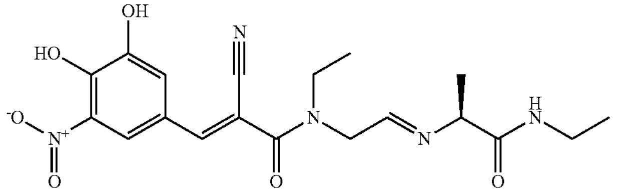 |

In some embodiments, $C_{1-4}$ alkylene refers to methylene, ethylene, propylene, isopropylene, butylene, or isobutylene.

In some embodiments, halo refers to one or more of fluorine, chlorine, bromine, or iodine. In some embodiments, $C_{1-4}$ haloalkyl refers to $C_{1-4}$ mono-, di-, or tri-haloalkyl. In some embodiments, $C_{1-4}$ haloalkyl refers to $C_{1-4}$ fluoroalkyl or $C_{1-4}$ chloroalkyl. In some embodiments, $C_{1-4}$ fluoroalkyl refers to $C_{1-4}$ monofluoroalkyl, $C_{1-4}$ difluoroalkyl, or $C_{1-4}$ trifluoroalkyl.

In some embodiments, heteroaryl refers to a $C_{3-15}$ heteroaryl (i.e. $C_{3-10}$ or $C_{3-9}$) group having one, two, three, four, five, or six heteroatoms independently selected from N, O, or S. In some embodiments, the heteroaryl is monocyclic. In some embodiments, the heteroaryl is bicyclic or tricyclic, the cyclic rings being fused or linked by a bond. In some embodiments, heteroaryl refers to furanyl, pyridinyl, pyrimidinyl, pyrazinyl, triazinyl, pyrrolyl, pyrazolyl, or imidazolyl.

In some embodiments, the compounds provided herein are selected from the compounds shown in Table 1, or a pharmaceutically acceptable salt thereof.

In some embodiments, provided herein are compositions, comprising one or more of the compounds provided herein. In some embodiments, the composition is a pharmaceutical composition further comprising a pharmaceutical acceptable carrier.

In some embodiments, the compounds or compositions provided herein may be housed within a container, optionally wherein the container reduces or blocks transmission of visible or ultraviolet light through the container. Compounds or compositions housed in such a container may degrade at a slower rate as compared to when housed in a container transparent to visible or ultraviolet light.

Compounds described herein also include isotopically-labeled compounds wherein one or more atoms is replaced by an atom having the same atomic number, but an atomic mass or mass number different from the atomic mass or mass number predominantly found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In some embodiments, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In some embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In some embodiments, the compounds described herein may be prepared by a method of synthesis that comprises any of the synthetic schemes shown in the Examples or in FIG. 1.

In some embodiments, reactive functional groups, such as hydroxyl, amino, imino, thio, or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In some embodiments, protective groups are removed by acid, base, reducing conditions (for example, by hydrogenolysis), or oxidative conditions. Groups such as trityl, dimethoxytrityl, acetal, and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

Methods

In some embodiments, provided herein are methods of inhibiting fat mass obesity-associated protein (FTO) activity in a cell, comprising contacting the cell with an effective amount of entacapone or a pharmaceutically acceptable salt thereof.

In some embodiments, provided herein are methods of inhibiting FTO activity in a cell, comprising contacting the cell with an effective amount of a compound provided herein.

In some embodiments, provided herein are methods of inhibiting FTO activity in a subject in need thereof, comprising administering to the subject an effective amount of entacapone or a pharmaceutically acceptable salt thereof.

In some embodiments, provided herein are methods of inhibiting FTO activity in a subject in need thereof, comprising administering to the subject an effective amount of a compound provided herein.

In some embodiments, provided herein are methods of inhibiting Notch1 activity in a cell, comprising contacting the cell with an effective amount of entacapone or a pharmaceutically acceptable salt thereof.

In some embodiments, provided herein are methods of inhibiting Notch1 activity in a cell, comprising contacting the cell with an effective amount of a compound provided herein.

In some embodiments, provided herein are methods of inhibiting Notch1 activity in a subject in need thereof, comprising administering to the subject an effective amount of entacapone or a pharmaceutically acceptable salt thereof.

In some embodiments, provided herein are methods of inhibiting Notch1 activity in a subject in need thereof, comprising administering to the subject an effective amount of a compound provided herein.

In some embodiments, provided herein are methods of treating a cancer in a subject in need thereof, comprising administering to the subject a therapeutically effective amount of entacapone or a pharmaceutically acceptable salt thereof.

In some embodiments, provided herein are methods of treating a cancer in a subject in need thereof, comprising administering to the subject a therapeutically effective amount of a compound provided herein.

In some embodiments of the methods described herein, the cancer is a glioblastoma. In some embodiments, the cancer is a diffuse intrinsic pontine glioma.

In some embodiments of the methods described herein, the cancer comprises a brain cancer or tumor, a leukemia, a breast cancer, a lung cancer, a colon cancer, a pancreatic cancer, an ovarian cancer, a prostate cancer, or a kidney cancer.

The compounds provided herein are useful in treating diseases associated with the RNA demethylase activity of FTO. Thus, in some embodiments, provided herein are methods of treating a systemic solid tumor, a metabolic disease, obesity, diabetes, or a neurodegenerative disorder.

In some embodiments, provided herein are methods of treating an FTO-related disease in a subject in need thereof, comprising administering to the subject a therapeutically effective amount of entacapone or a pharmaceutically acceptable salt thereof.

In some embodiments, provided herein are methods of treating an FTO-related disease in a subject in need thereof, comprising administering to the subject a therapeutically effective amount of a compound provided herein.

In some embodiments, provided herein are methods of treating Notch1-related disease in a subject in need thereof, comprising administering to the subject a therapeutically effective amount of entacapone or a pharmaceutically acceptable salt thereof.

In some embodiments, provided herein are methods of treating a Notch1-related disease in a subject in need thereof, comprising administering to the subject a therapeutically effective amount of a compound provided herein.

In some embodiments of these methods, the administered compound is a compound of Table 1 or a pharmaceutically acceptable salt thereof. In some embodiments of these methods, the methods comprise administration or use of a compound selected from compound 31 or a pharmaceutically acceptable salt thereof.

In some embodiments of these methods, the compound is administered or provided as a composition. In some embodiments, the compound is administered or provided as a pharmaceutical composition further comprising a pharmaceutically acceptable carrier.

In some embodiments of these methods, the entacapone or pharmaceutically acceptable salt thereof is administered or provided as a composition. In some embodiments, the entacopone or pharmaceutically acceptable salt thereof is administered or provided as a pharmaceutical composition further comprising a pharmaceutically acceptable carrier.

In some embodiments of these methods, the FTO-related disease is obesity, diabetes, Alzheimer's disease, or a cancer.

In some embodiments of the methods provided herein, the cancer is a brain tumor. In some embodiments, the cancer is a glioblastoma. In some embodiments, the cancer is a breast cancer, leukemia, brain tumor, or lung cancer. In some embodiments, the breast cancer is triple-negative breast cancer. In some embodiments, the lung cancer is non-small cell lung cancer.

In some embodiments, the cell is a brain cell. In some embodiments, the cell is a glioma stem cell. In some embodiments, the cell contacting is in a subject. In some embodiments, the cell contacting is in vitro. In some embodiments, the cell is a cell that originated as a hematapoietic stem cell (e.g., a blood cell), a breast cell, a lung cell, a colon cell, a pancreatic cell, an ovarian cell, a prostate cell, or a kidney cell. In some embodiments, the blood cell is a multipotential stem cell. In some embodiments, the multipotential stem cell is a lymphoid progenitor cell or a myeloid progenitor cell. In some embodiments, the lymphoid progenitor cell is a natural killer cell, a T lymphocyte, or a B lymphocyte. In some embodiments, the myeloid progenitor cell is a neutrophil, a basophil, an eosinophil, a monocyte, a platelet, or an erythrocyte. In some embodiments, the monocyte is a macrophage.

The subject considered herein is typically a human. However, the subject can be any mammal for which treatment is desired. Thus, the methods described herein can be applied to both human and veterinary applications.

In some embodiments of these methods, the active agent that is administered may be administered in combination with a second active agent that may be any compound described herein, or the second active agent may be selected from any agent suitable for one of the uses described herein.

In some embodiments of these methods, the active agent(s) is provided in a form suitable for the desired route of administration, which may vary as circumstances require. For example, in some embodiments, oral administration may be utilized, and the agent may be formulated as a solid dosage form, a gel, a liquid, a paste, a spray, or another suitable form for oral administration. In some embodiments, the administration is oral administration, pulmonary administration, or intravenous administration. In some embodiments, the administration is global and the compound crosses the blood brain barrier to impart its activity. In some embodiments, the administration is local injection. In some embodiments, the administration is intracerebral administration. In some embodiments, the administration is intracranial administration.

In some embodiments, the subject comprises a refractory disease. In some embodiments, the refractory disease comprises a refractory cancer.

Administration/Dose

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual compounds, and can generally be estimated based on $EC_{50}$ values found to be effective in in vitro and in vivo animal models. In general, dosages may range from 0.01 μg to 1 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent recurrence of the disease state, wherein the compound(s) is administered in maintenance doses, ranging from 0.01 μg to 1 g/kg of body weight, once or more daily, to once every 20 years.

In some embodiments, the compound(s) described herein is administered alone, that is, without another, different, active agent. In some embodiments, the compound(s) described herein is administered in combination with another (i.e. one or more), different, active agent(s).

In some embodiments of these methods, the active agent(s) is provided in a form suitable for the desired route of administration, which may vary as circumstances require. For example, in some embodiments, oral administration may be utilized, and the agent may be formulated as a solid dosage form, a gel, a liquid, a paste, a spray, or another suitable form for oral administration. In some embodiments, the administration is oral administration, pulmonary administration, or intravenous administration. In some embodiments, the administration is global and the compound crosses the blood brain barrier to impart its activity. In some embodiments, the administration is local injection. In some embodiments, the administration is intracerebral administration. In some embodiments, the administration is intracranial administration.

In some embodiments, the compound is administered in a therapeutically effective amount or dosage. The amount of the compound that corresponds to a therapeutically effective amount is strongly dependent on the type of disease, stage of the disease, the age of the patient being treated, and other factors.

While the amounts of the compounds described herein should result in effective treatment of a particular disease described herein, the amounts administered are preferably not excessively toxic to the patient (i.e., the amounts are preferably within toxicity limits as established by medical guidelines). In some embodiments, either to prevent excessive toxicity or provide a more efficacious treatment of a disease described herein, or both, a limitation on the total administered dosage is provided. Typically, the amounts considered herein are per day. However, half-day and two-day or three-day cycles also are contemplated.

Different dosage regimens may be used for treatment. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage amount is administered every other day.

Compounds described herein, or their pharmaceutically acceptable salts, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracistemally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents. Isotonic agents may also be included. Prolonged absorption of an injectable pharmaceutical form can be brought about by the use of agents delaying absorption. Auxiliary agents also can include wetting agents, emulsifying agents, pH buffering agents, and antioxidants.

Solid dosage forms can be prepared with coatings and shells, such as enteric coatings and others well-known in the art. They can contain pacifying agents and can be of such composition that they release the active agents (i.e. compound(s) described herein) in a certain part of the intestinal tract in a delayed manner. The compounds described herein can also be in microencapsulated form, if appropriate, with one or more of the above-mentioned carriers.

Liquid dosage forms for oral administration include pharmaceutically acceptable emulsions, solutions, suspensions, syrups, and elixirs. Such dosage forms are prepared, for example, by dissolving, dispersing, etc., the compound(s) described herein and optional pharmaceutical carrier(s) to thereby form a solution or suspension.

Generally, depending on the intended mode of administration, the pharmaceutically acceptable compositions will contain about 1% to about 99% by weight of the compound described herein and 99% to 1% by weight of a pharmaceutically acceptable carrier. In one example, the composition may be between about 5% and about 75% by weight of a compound described herein with the rest being suitable pharmaceutical carriers.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits include package(s) comprising a compound, or combinations thereof, or compositions described herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, and any packaging material suitable for a selected formulation and intended mode of administration and treatment.

The kit can also include additional items with the package, either attached to the outside of the package or disposed within the package, for example, pipettes.

Kits can further contain instructions for approved uses and for administering the compound(s) described herein to a patient. Kits can also contain labeling or product inserts for the compounds. The kits can include active agents in the solid phase or in a liquid phase in a package. The kits can also include buffers for preparing solutions for conducting the methods described herein, and pipettes for transferring liquids from one container to another.

Definitions

Certain terms, whether used alone or as part of a phrase or another term, are defined below.

The articles "a" and "an" refer to one or to more than one of the grammatical object of the article.

Numerical values relating to measurements are subject to measurement errors that place limits on their accuracy. For this reason, all numerical values provided herein, unless otherwise indicated, are to be understood as being modified by the term "about." Accordingly, the last decimal place of a numerical value provided herein indicates its degree of accuracy. Where no other error margins are given, the maximum margin is ascertained by applying the rounding-off convention to the last decimal place or last significant digit when a decimal is not present in the given numerical value.

The term "alkyl" refers to branched or straight chain saturated hydrocarbon.

As used herein, the term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

The term "aryl" refers to a carbocyclic aromatic system comprising one, two, three, or more rings.

The term "$C_{n-m}$" refers to a moiety comprising n to m carbon atoms, wherein n and m are integers.

The term "cycloalkyl" refers to an alkyl moiety comprising a cyclic alkyl moiety comprising one, two, three, or more rings.

The terms "composition" and "pharmaceutical composition" refer to a mixture of at least one compound described herein with a pharmaceutically acceptable carrier. The pharmaceutical composition facilitates administration of the compound to a patient or subject. Multiple techniques of administering a compound exist including, but not limited to, intravenous, oral, aerosol, parenteral, ophthalmic, pulmonary, and topical administration.

As used herein, an "effective amount" or "therapeutically effective amount" refers to an amount of therapeutic compound, such as a compound described herein, administered to a subject, either as a single dose or as part of a series of doses, which is effective to produce a desired therapeutic effect. In general, the therapeutically effective amount can be estimated initially either in cell culture assays or in mammalian animal models, for example, in non-human primates, mice, rabbits, dogs, or pigs. The animal model may also be used to determine the appropriate concentration range and route of administration. Such information can then be used to determine useful doses and routes for administration in non-human subjects and human subjects.

The term "haloalkyl" refers to an alkyl moiety substituted with one or more halogens.

The terms "halogen" and "halo" refer to one or more atoms independently selected from F, Br, Cl, or I.

The term "heteroaryl" refers to an aryl moiety comprising at least one ring heteroatom selected from O, S, or N, wherein each ring may comprise, independently, one, two, three, or four ring heteroatoms independently selected from O, S, or N.

The term "heterocycloalkyl" refers to an alkyl moiety comprising a cyclic alkyl moiety comprising one, two, three, or more rings, and at least one heteroatom selected from O, S, or N, wherein each ring may comprise one, two, three, or four ring heteroatoms independently selected from O, S, or N.

As used herein, the phrase "package" means any vessel suitable to contain compounds or compositions described herein.

The term "pharmaceutically acceptable carrier" means a pharmaceutically acceptable material, composition or carrier, such as a liquid filler, solid filler, stabilizer, dispersing agent, suspending agent, diluent, excipient, thickening agent, solvent, or encapsulating material, involved in carrying or transporting at least one compound described herein within or to the patient such that the compound may perform its intended function. A given carrier must be "acceptable" in the sense of being compatible with the other ingredients of a particular formulation, including the compounds described herein, and not injurious to the patient. Other ingredients that may be included in the pharmaceutical compositions described herein are known in the art and described, for example, in "Remington's Pharmaceutical Sciences" (Genaro (Ed.), Mack Publishing Co., 1985), the entire content of which is incorporated herein by reference.

As used herein, the term "pharmaceutically acceptable salts" refers to derivatives of the compounds described herein wherein the parent compound is modified by converting an existing acid or base moiety to its salt form. Lists of suitable salts are found in Remington's Pharmaceutical Sciences, 17th ed., Mack Publishing Company, Easton, Pa., 1985, p. 1418, and Journal of Pharmaceutical Science, 66, 2 (1977), each of which is incorporated herein by reference in its entirety.

The term "refractory disease" refers to a disease that continues to progress during treatment with a pharmaceutical ingredient other than the compounds provided herein, partially responds to the other treatment, or transiently responds to the other treatment. The term may be applied to each of the diseases referred to herein.

As used herein, the term "treatment" refers to the application of one or more specific procedures used for the amelioration of a disease. In certain embodiments, the specific procedure is the administration of one or more pharmaceutical agents. "Treatment" of an individual (e.g. a mammal, such as a human, a domesticated pet, or a livestock) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset.

EXAMPLES

The following Examples further illustrate aspects of the compounds and methods provided herein. However, these Examples are in no way a limitation of the teachings or disclosure as set forth herein. These Examples are provided for illustration purposes. Unless otherwise noted, all starting materials in the synthetic preparation procedures provided herein were obtained from commercial suppliers and used without purification.

Example 1: High FTO Expression Correlates with Aggressive GSC Phenotype

To examine whether fat mass and obesity-associated protein (FTO) expression correlates with glioma stem cell (GSC) phenotype, raw transcriptomic data from 44 GSCs were clustered for high- and low-expression of FTO using median expression cut-off. Differential expression analysis between high and low FTO groups was conducted using DEseq at FC of 1.5 and $p<0.05$. Differential analysis was performed on top and bottom 25% FTO-expressing samples. 11 high-expressing FTO samples were compared to 11 low-expressing samples. KEGG pathway enrichment was conducted on upregulated genes in the high FTO group, and significant functional categories found were: FoxO signaling; regulating pluripotency of stem cells; sphingolipid metabolism; ether lipid metabolism; and phospholipase D signaling metabolism.

Next, gene set enrichment analysis was performed on 22 high and 22 low FTO expressing GSCs. The hallmark gene set signatures were used to assess differences in high versus low FTO GSCs groups. The top 10 upregulated gene sets are listed in Table 2.

TABLE 2

| Hallmark Gene Set | False Discovery Rate (FDR) |
|---|---|
| Angiogenesis | 0.00419 |
| Epithelial Mesenchymal Transition | 0.21239 |
| Myogenesis | 0.31309 |
| Protein Secretion | 0.26141 |
| Hedgehog Signaling | 0.27169 |
| WNT Beta Catenin Signaling | 0.24102 |
| Apical Junction | 0.26109 |
| Notch Signaling | 0.25433 |
| UV Response DN | 0.34614 |
| IL6 JAK STAT3 Signaling | 0.31672 |

The epithelial mesenchymal transition signature set was highly enriched at nominal p-values<0.01. These data indicated that high FTO expression correlates with aggressive GSC phenotype.

Example 2: FTO Inhibitor Entacapone Inhibits GSC Self-Renewal

To examine whether treatment with Entacapone affects the ability of GSCs to self-renew, serial dilutions of GSCs were cultured from two patients with glioblastoma in the presence of 40 μM entacapone or DMSO (Control) for 14 days. 40 μM dose of entacapone corresponded to 120 mg of the dry drug, which is significantly lower than the daily dose currently approved for the treatment of Parkinson's (800-1600 mg). This showed that entacapone significantly decreased the tumor-sphere formation frequency of GSCs from two patients with glioblastoma as examined by in vitro extreme limiting dilution analysis (ELDA), a method widely used to determine self-renewal capacity of stem cells.

Example 3: Virtual Screening of Compound Activity

Molecular dynamics and binding free energy calculations were used to assess propensity of FTO inhibition for selected compounds provided herein. GBVI/WSA dG for selected compounds provided herein, and are listed in Table 3.

An rsynth value was also determined for selected compounds provided herein, and are listed in Table 3. The rsynth value is a calculated synthetic feasibility score. The synthetic feasibility score is the fraction of the atoms of a new structure that ultimately appear in a retrosynthetic fragment found in a starting materials database. A value of one (1) indicates that the molecule is very likely synthesizable. As an rsynth value approaches 0, the likelihood of being synthesizable, or ease of synthesis, diminishes. That is, the difficulty of synthesizing a compound is expected to increase as the rsynth value approaches 0.

MOE Dock (Molecular Operating Environment (MOE), 2018.01; Chemical Computing Group Inc., 1010 Sherbooke St. West, Suite #910, Montreal, QC, Canada, H3A 2R7. 2018.) was used for molecular docking of proteins with entacapone. The crystal structure of FTO was downloaded from RSDB (PDB CODE: 3LFM), the 2D structure of molecules were drawn from ChemBioDraw and converted to 3D in MOE through energy minimization. Then the protonation state of target and the orientation of the hydrogens were optimized by QuickPrep module, at the PH of 7.0 and temperature of 300 K. Prior to docking, the force field of AMBER10: EHT and the implicit solvation model of Reaction Field (R-field) were selected. The binding site of FTO was identified according to the reference (Han, Z.; Niu, T.; Chang, J.; Lei, X.; Zhao, M.; Wang, Q.; Cheng, W.; Wang, J.; Feng, Y.; Chai, J., Crystal structure of the FTO protein reveals basis for its substrate specificity. Nature 2010, 464 (7292), 1205-9), native ligand 3DT was defined as the binding site. The docking workflow followed the "induced fit" protocol, in which the side chains of the receptor pocket were allowed to move according to ligand conformations, with a constraint on their positions. The weight used for tethering side chain atoms to their original positions was 10. All docked poses of molecules were ranked by London dG scoring first, then a force field refinement was carried out on the top 30 poses followed by a rescoring of GBVI/WSA dG. The best ranked pose was selected as the final binding mode.

Analysis of the binding modes of compounds with native ligand was performed using the structure-based drug design module in MOE. Compounds were minimized and ranged by GBVI/WSA dG.

TABLE 3

Calculated GBVI/WSA dG and rsynth values of selected compounds provided herein.

| Compound # | rsynth | GBVI/WSA dG |
|---|---|---|
| 1 | 0.17857143 | −8.1704359 |
| 2 | 0.1875 | −8.1552172 |
| 3 | 0.18518518 | −8.1393423 |
| 4 | 0.23333333 | −8.1300077 |
| 5 | 0.41379312 | −8.1147308 |
| 6 | 0.1875 | −8.1076431 |
| 7 | 0.25925925 | −8.1075373 |
| 8 | 0.29032257 | −8.0818815 |
| 9 | 0.16666667 | −8.0660744 |

TABLE 3-continued

Calculated GBVI/WSA dG and rsynth values of selected compounds provided herein.

| Compound # | rsynth | GBVI/WSA dG |
|---|---|---|
| 10 | 0.32258064 | −8.0619841 |
| 11 | 0.43333334 | −8.0528965 |
| 12 | 0.19354838 | −8.0496616 |
| 13 | 0.16666667 | −8.0480585 |
| 14 | 0.36666667 | −8.0456123 |
| 15 | 0.25 | −8.0336866 |
| 16 | 0.3548387 | −8.0334063 |
| 17 | 0.25 | −8.0316763 |
| 18 | 0.1724138 | −8.0280485 |
| 19 | 0.16666667 | −8.0271845 |
| 20 | 0.3548387 | −8.025218 |
| 21 | 0.3548387 | −8.0239983 |
| 22 | 0.25 | −8.0236864 |
| 23 | 0.43333334 | −8.0225067 |
| 24 | 0.23333333 | −8.0172281 |
| 25 | 0.39285713 | −8.0139961 |
| 26 | 0.36666667 | −8.0070286 |
| 27 | 0.32258064 | −8.0047941 |
| 28 | 0.26666668 | −8.0045528 |
| 29 | 0.21428572 | −8.0042524 |
| 30 | 0.1724138 | −8.0037441 |
| 31 | 0.3704 | −7.9887 |
| 32 | 0.1724 | −7.9987 |
| 33 | 0.2333 | −7.9977 |
| 34 | 0.2000 | −7.9925 |
| 35 | 0.2069 | −7.9899 |
| 36 | 0.1786 | −7.9912 |
| 37 | 0.2667 | −7.9895 |

Example 4: Entacapone Inhibits Expression of Cancer Stem Cell Genes

GSCs were treated with 40 UM entacapone for 48 hours to assess whether entacapone would affect expression of stemness-related transcripts. A qPCR array for 84 validated cancer stem cell markers was performed (Qiagen-RT-profiler PCR arrays). It was discovered that treatment with entacapone resulted in significant inhibition of several cancer stem cell transcripts (FIG. 1).

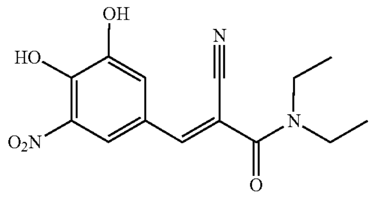

Entacapone

Example 5: GSC Invasion Live Imaging

Figure 2:
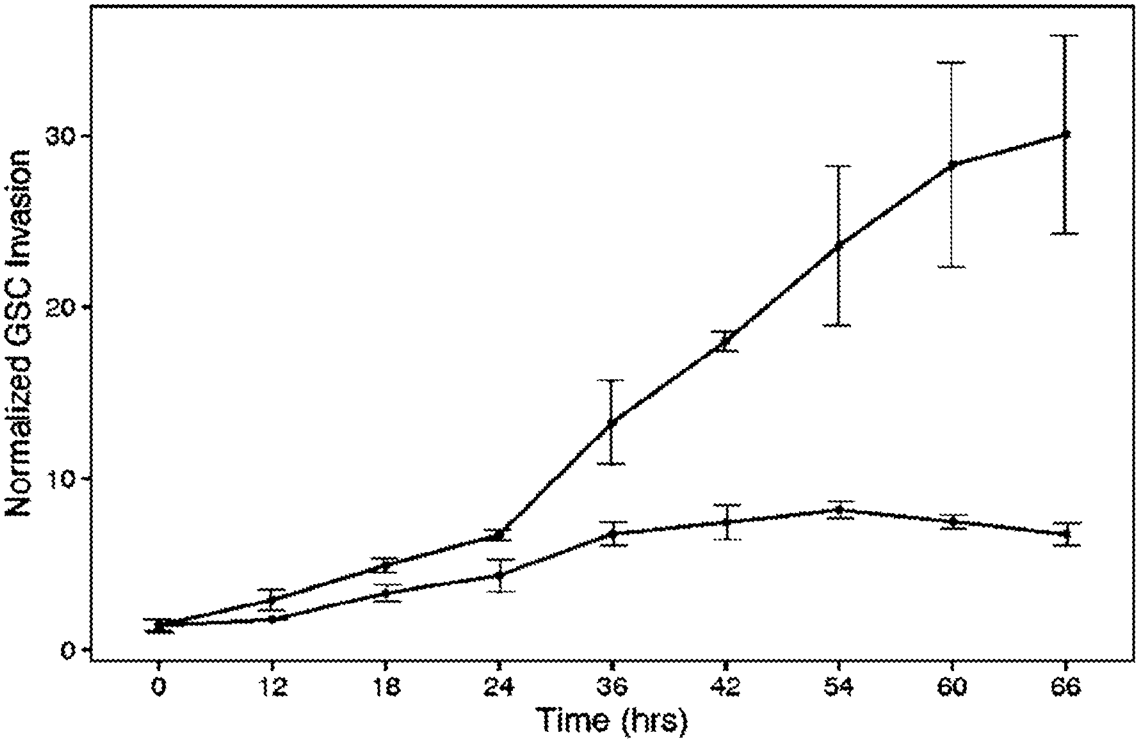
FIG. 2 shows normalized GSC invasion area over 66 hours of live imaging following entacapone treatment (upper line is DMSO, lower line is 40 UM entacapone).

GSCs in Matrigel 3D matrix, were treated with 40 UM entacapone or DMSO (control) and live imaging was performed in regular time intervals using the Incucyte live cell imaging system. Normalized area of invasion was quantified following normalization of the invading area with the area occupied by the GSC sphere. FIG. 2 shows normalized GSC invasion area over 66 hours of live imaging following entacapone treatment. These data show that entacapone inhibits invasion of GSCs.

Example 6: Assessment of Gene Expression Correlated with FTO Expression

A set of stem relevant genes was collected from the cancer stemness panel. Using the TCGA HG-UG133A affymetrix platform, these genes were assessed for correlation against FTO expression. Significant correlation of FTO with Notch1 expression in GSCs was observed (R=0.53, p-val=1.13e-39).

Example 7: Notch1 Inhibition Assay

Figure 3:
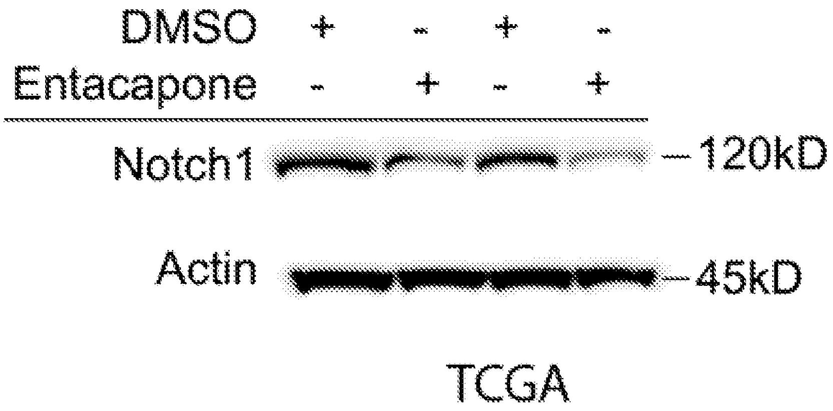
FIG. 3 shows inhibition of Notch1 protein expression induced by entacapone as described by Example 7.

To determine whether inhibition of FTO with entacapone results in inhibition of Notch1 protein expression in GSCs, GSCs from two patients with glioblastoma (two different GSC lines) were treated with 40 UM entacapone for 48 hours, and Western Blot for Notch1 were performed (FIG. 3). These data show that entacapone induces inhibition of Notch1 protein expression.

Example 8: Synthetic Preparation of Common Core Intermediate

The compounds provided herein include a common core moiety,

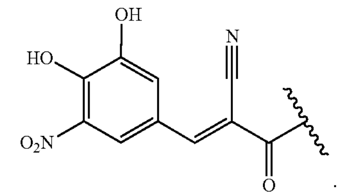 [SMILES: *C(=O)/C(C#N)=C/c1cc(O)c(O)c([N+](=O)[O-])c1]

Figure 4:
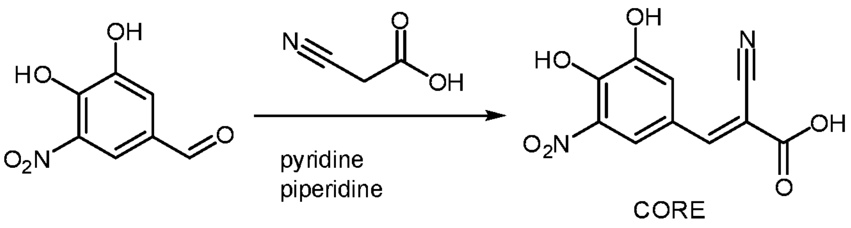
FIG. 4 shows a synthetic scheme of the common core intermediate (CORE) described in Example 8.

Synthetic preparation of the compounds provided herein include use of the common core intermediate (E)-2-cyano-3-(3,4-dihydroxy-5-nitrophenyl) acrylic acid (CORE). A synthetic scheme of the CORE is shown in FIG. 4, and described here.

A solution of 3,4-dihydroxy-5-nitrobenzaldehyde (10.0 g, 54.6 mmol), 2-cyanoacetic acid (9.4 g, 109.2 mmol) and piperidine (3 mL) in pyridine (50 mL) was heated at 90° C. overnight. The mixture was concentrated to dryness and the residue washed with acetone (50 mL) and EtOAc (30 mL×2) to afford (E)-2-cyano-3-(3,4-dihydroxy-5-nitrophenyl) acrylic acid (5.5 g, 40%) as a yellow solid. The compound was characterized by LC/MS and $^1$H NMR spectroscopies.

Example 9: Synthetic Preparation of Compound 1

Figure 5:
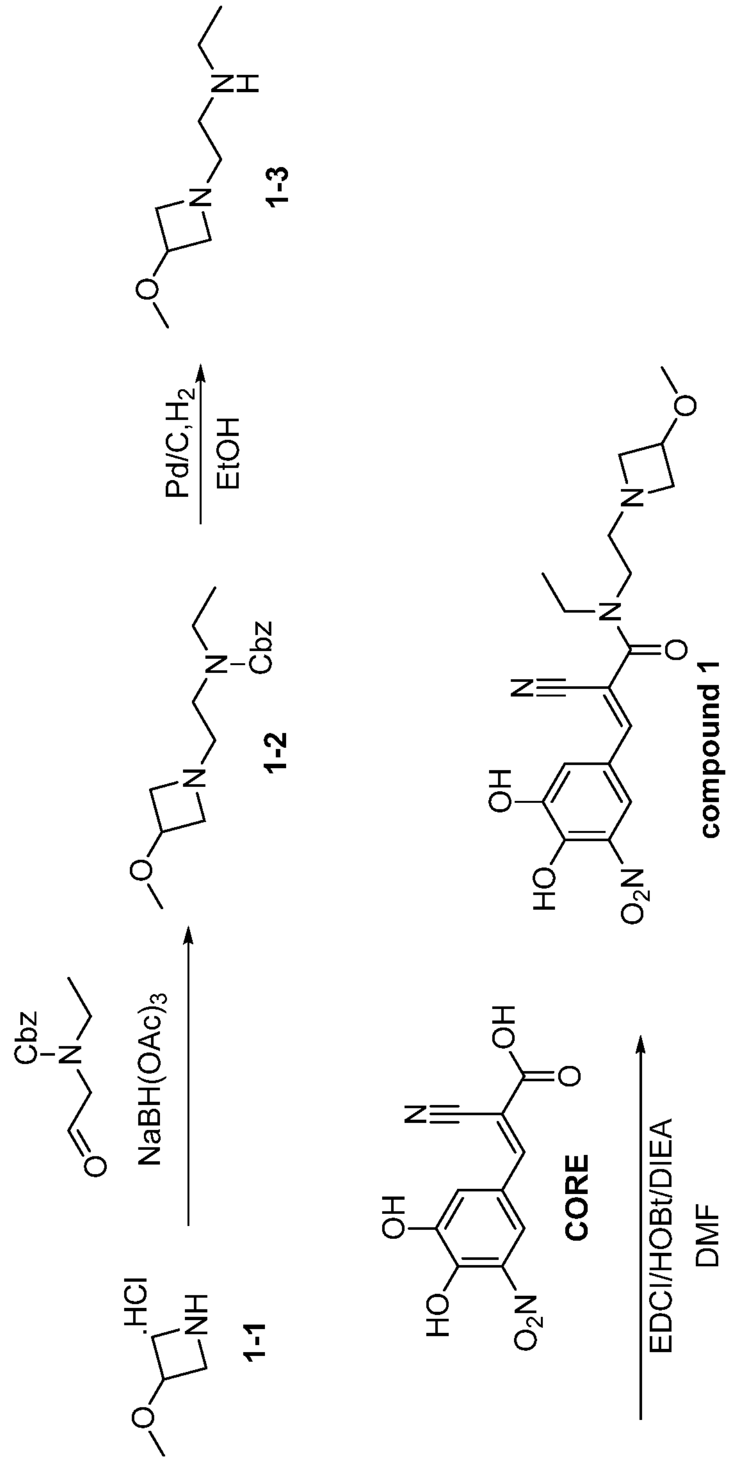
FIG. 5 shows synthetic schemes for Compound 1 described in Example 9.

Compound 1 is prepared according to the synthetic schemes shown in FIG. 5, and as described below.

Synthesis of compound 1-2: To a solution of compound 1-1 (846 mg, 4.52 mmol) in MeOH (20 mL) was added TEA (457 mg, 4.52 mmol) and the mixture was stirred at RT for 20 min. Benzyl ethyl(2-oxoethyl) carbamate (1.00 g, 4.52 mmol) was added and stirring was continued for 3 h. Sodium triacetoxyborohydride (3.84 g, 18.2 mmol) was added and stirring was continued at RT for 16 h. The mixture was poured into cold water (50 mL), extracted with EtOAc (30 mL×3) and the combined organic phases washed with water (100 mL), brine (100 mL), dried over $Na_2SO_4$ and concentrated under reduced pressure. The residue was purified by silica gel chromatography (DCM/MeOH=50/1, v/v) to afford compound 1-2 (1.20 g, 52%) as a colorless oil. The compound was characterized by LC/MS and $^1$H NMR spectroscopies.

Synthesis of compound 1-3: To a solution of compound 1-2 (500 mg, 1.71 mmol) in ethanol (5 mL) was added 10% Pd/C (200 mg) and the mixture was heated at 60° C. for 16 h under a $H_2$ atmosphere. The mixture was filtered, and the filtrate concentrated under reduced pressure. The residue was purified by silica gel chromatography (DCM/MeOH=20/1, v/v) to afford compound 1-3 (200 mg, 74%) as colorless oil. The compound was characterized by LC/MS and $^1$H NMR spectroscopies.

Synthesis of compound 1: To a solution of (E)-2-cyano-3-(3,4-dihydroxy-5-nitrophenyl) acrylic acid (316 mg, 1.26 mmol) and DIPEA (489 mg, 3.78 mmol) in dry DMF (5 mL) at 0° C. was added HOBT (204 mg, 1.51 mmol) and EDCI·HCl (363 mg, 1.89 mmol) and the mixture was stirred for 30 min. A solution of compound 1-3 (200 mg, 1.26 mmol) in dry DMF (2 mL) was then added and stirring was continued at RT for 16 h. The mixture was purified directly by C18, RP column (Biotage, ACN/$H_2O$=20%, buffered with 0.1% HCOOH) followed by prep-HPLC (Agilent 10 prep-C18, 10 μm, 250×21.2 mm column, eluting with a gradient of MeCN in water with 0.1% formic acid, at a flow rate of 20 mL/min) to give compound 1 (52.0 mg, 11%) as a red solid. The compound was characterized by LC/MS and $^1$H NMR spectroscopies.

Example 10: Synthetic Preparation of Compound 20

Figure 6:
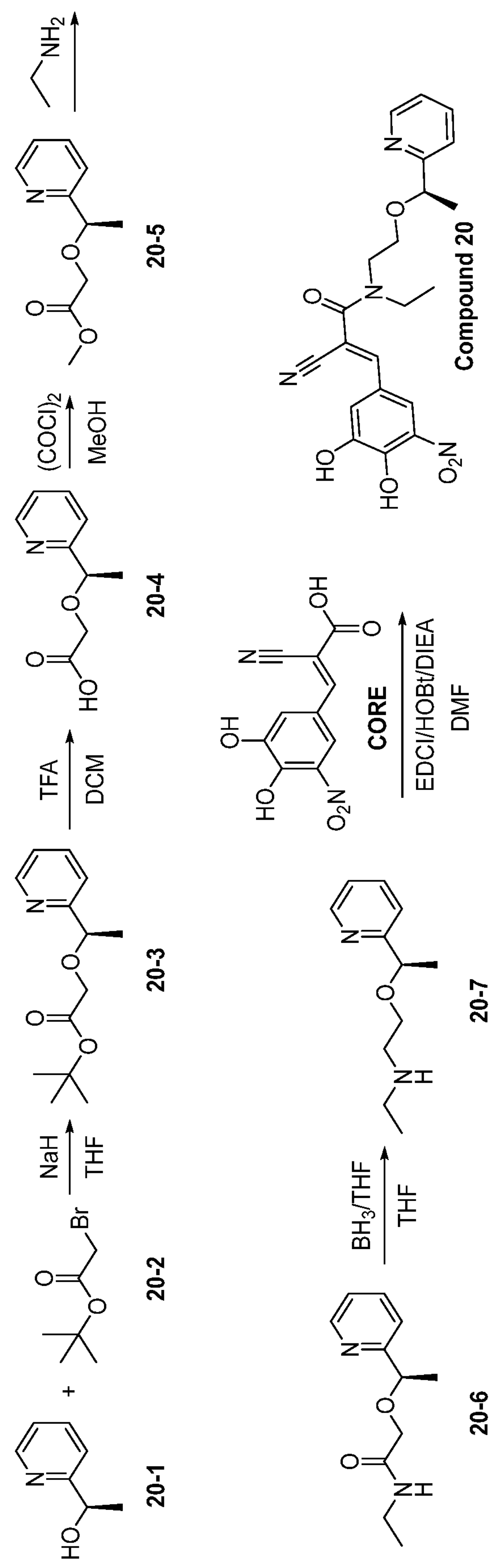
FIG. 6 shows synthetic schemes for Compound 20 described in Example 10.

Compound 20 is prepared according to the synthetic schemes shown in FIG. 6, and as described below.

Synthesis of 20-3: To a suspension of NaH (60% suspension in oil, 438 mg, 18.3 mmol) in THF (15 mL) at 0° C. was added a solution of compound 20-1 (1.50 g, 12.2 mmol) in THF (2 mL) drop-wise and the mixture was heated at 70° C. for 1 h. The mixture was allowed to cool to RT, compound 20-2 (2.61 g, 13.4 mmol) was added and stirring was continued at RT for 16 h. The mixture was poured into cold water (50 mL), extracted with EtOAc (30 mL×2) and the combined organic extracts washed with water (50 mL), brine (100 mL), dried over $Na_2SO_4$ and concentrated to dryness. The residue was purified by silica gel chromatography (Petroleum ether/EtOAc=30/1, v/v) to afford compound 20-3 (2.50 g, 87%) as a colorless oil. The compound was characterized by LC/MS and $^1$H NMR spectroscopies.

Synthesis of 20-4: To a solution of compound 20-3 (2.50 g, 10.5 mmol) in DCM (5 mL) was added TFA (3.60 g, 31.6 mmol) drop-wise and the mixture was heated at 400° C. for 3 h. The mixture was concentrated to dryness to afford compound 20-4 (1.80 mg, 88%) as yellow oil, which was used directly in the next step.

Synthesis of 20-5: To a solution of compound 20-4 (1.50 g, 8.28 mmol) in MeOH (5 mL) at 0° C. was added oxalyl chloride (1.4 mL, 16.6 mmol) drop-wise and the mixture was stirred at RT for 2 h. The mixture was concentrated to dryness to afford compound 20-5 (1.30 mg, 80%) as yellow oil, which was used directly in the next step.

Synthesis of 20-6: To a solution of compound 20-5 (1.30 g, 6.66 mmol) in THF (2 mL) was added a 2 M solution of ethylamine in THF (35 mL) and the mixture was heated at 80° C. for 16 h in a sealed tube. The mixture was concentrated to dryness and the residue purified by silica gel chromatography (Petroleum ether/EtOAc=20/1, v/v) to afford compound 20-6 (1.10 g, 79%) as a yellow oil. The compound was characterized by LC/MS and $^1$H NMR spectroscopies.

Synthesis of 20-7: To a solution of compound 20-6 (500 mg, 2.40 mmol) in dry THF (5 mL) sat −20° C. was added Borane-tetrahydrofuran complex (12.0 mL, 24.0 mmol) slowly via syringe and the mixture was allowed to warm to RT and stirred overnight. The reaction was carefully quenched by addition of methanol (2 mL) and 1 M aqueous HCl (10 mL) and the mixture was stirred at RT for 2 h then concentrated to dryness. The residue was diluted with a saturated aqueous Na2CO3 solution (10 mL), extracted with EtOAc (30 mL×3) and the combined organic layers dried over Na2SO4 and concentrated to dryness to afford compound 20-7 (348 mg, 75%) as colorless oil. The compound was characterized by LC/MS and $^1$H NMR spectroscopies.

Synthesis of compound 20: To a solution of (E)-2-cyano-3-(3,4-dihydroxy-5-nitrophenyl) acrylic acid (322 mg, 1.29 mmol) and DIPEA (333 mg, 2.57 mmol) in DMF (5 mL) was added HOBT (209 mg, 1.54 mmol) and EDCI·HCl (370 mg, 1.93 mmol) and the mixture was stirred for 30 min. A solution of compound 20-7 (250 mg, 1.29 mmol) in DMF (1 mL) was then added and stirring was continued at RT overnight. The mixture was diluted with water (50 mL), extracted with EtOAc (30 mL×2) and the combined organic layers washed with brine (50 mL×2), dried over Na2SO4 and concentrated under reduced pressure. The residue was purified by prep-HPLC (Agilent 10 prep-C18, 10 μm, 250×21.2 mm column, eluting with a gradient of MeOH in water with 0.1% formic acid, at a flow rate of 20 mL/min) to afford compound 5 (72.9 mg, 13%) as a red solid. The compound was characterized by LC/MS and $^1$H NMR spectroscopies.

Example 11: Synthetic Preparation of Compound 29

Figure 7:
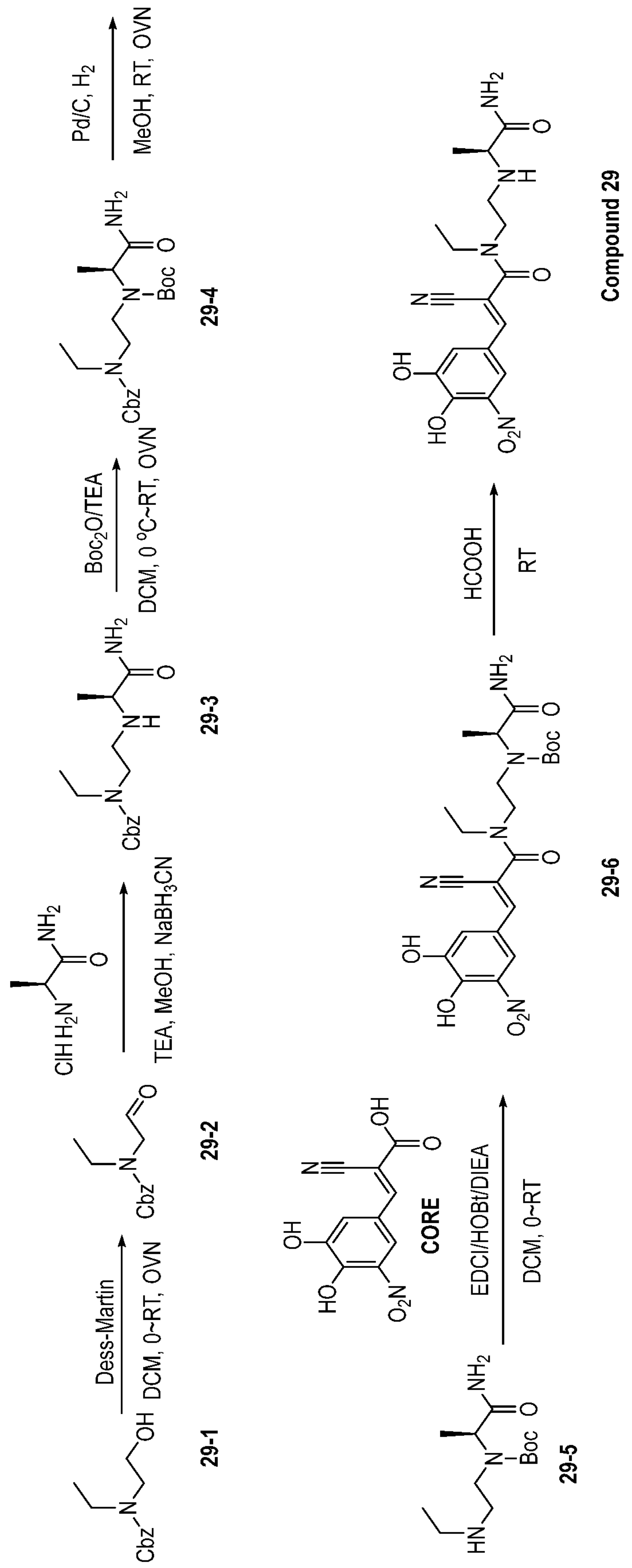
FIG. 7 shows synthetic schemes for Compound 29 described in Example 11.

Compound 29 is prepared according to the synthetic schemes shown in FIG. 7, and as described below.

Synthesis of compound 29-2: To a solution of compound 29-1 (5.0 g, 22.4 mmol) in DCM (15 mL) at 0° C. was added Dess-Martin reagent (11.4 g, 26.9 mmol) and the mixture was allowed to warm to RT and stirred overnight. The mixture was filtered and the filtrate concentrated under reduced pressure. The residue was purified by silica gel chromatography (Petroleum ether/EtOAc=5/1, v/v) to give compound 29-2 (3.9 g, 79%) as a light yellow oil. The compound was characterized by LC/MS and $^1$H NMR spectroscopies.

Synthesis of compound 29-3: To a solution of L-Alaninamide Hydrochloride (2.2 g, 17.62 mmol) in MeOH (10 mL) was added TEA (1.8 g, 17.6 mmol) and the mixture was stirred at RT for 10 min. Compound 29-2 (3.9 g, 17.6 mmol) was added and stirred for 1 h before adding Na(CN)3BH (4.4 g, 70.5 mmol). Then the mixture was stirred overnight. The reaction was quenched by addition of water (50 mL) and the mixture extracted with EtOAc (40 mL×3). The combined organic layers were washed with water (100 mL×3), brine (50 mL), dried over $Na_2SO_4$ and concentrated under reduced pressure. The residue was purified by silica gel chromatography (DCM/MeOH=20/1, v/v) to give compound 29-3 (2.4 g, 46%) as a yellow oil. The compound was characterized by LC/MS and $^1$H NMR spectroscopies.

Synthesis of compound 29-4: To a solution of compound 29-3 (2.4 g, 8.18 mmol) and TEA (2.48 g, 24.5 mmol) in DCM (15 mL) at 0° C. was slowly added $Boc_2O$ (3.85 g, 16.4 mmol) and the mixture was stirred at RT overnight. The mixture was diluted with water, extracted with DCM (40 mL×3) and the combined organic layers were washed with water (50 mL×3), brine (50 mL), dried over $Na_2SO_4$ and concentrated under reduced pressure. The residue was purified by silica gel chromatography (DCM/MeOH=20/1, v/v) to give compound 29-4 (1.9 g, 59%) as a light yellow oil. The compound was characterized by LC/MS and $^1$H NMR spectroscopies.

Synthesis of compound 29-5: A mixture of compound 29-4 (1.9 g, 5.59 mmol) and 10% Pd/C (220 mg, 2.07 mmol) in MeOH was stirred at RT under $H_2$ atmosphere overnight. The mixture was filtered and the filtrate concentrated under reduced pressure. The residue was purified by silica gel chromatography (DCM/MeOH=10/1, buffered with 0.1% $NH_3 \cdot H_2O$) to give compound 29-5 (350 mg, 28%) as a light yellow oil. The compound was characterized by LC/MS and $^1$H NMR spectroscopies.

Synthesis of compound 29-6: To a solution of (E)-2-cyano-3-(3,4-dihydroxy-5-nitrophenyl) acrylic acid (337.5 mg, 1.35 mmol) and DIPEA (523.6 mg, 4.05 mmol) in DCM (10 mL) at 0° C. was added HOBT (218.9 mg, 1.62 mmol) and EDCI·HCl (388.2 mg, 2.03 mmol). The mixture was stirred for 30 min. A solution of compound 29-5 (350 mg, 1.35 mmol) in DCM (3 mL) was added and the mixture was allowed to warm to RT and stirred overnight. The mixture was concentrated under reduced pressure and the residue purified by silica gel chromatography (DCM/MeOH=10/1, v/v) followed by prep-HPLC (Agilent 10 prep-C18, 10 μm, 250×21.2 mm column, eluting with a gradient of MeCN in water with 0.1% formic acid, at a flow rate of 20 mL/min) to give compound 29-6 (40 mg, 6%) as a red oil. The compound was characterized by LC/MS and $^1$H NMR spectroscopies.

Synthesis of compound 29: A solution of compound 29-6 (40 mg 0.08 mmol) in HCOOH (2 mL) was stirred at RT for 3 h, then concentrated under reduced pressure to give compound 22 (29 mg, 60%) as a red solid. The compound was characterized by LC/MS and $^1$H NMR spectroscopies.

Example 12: Synthetic Preparation of Compound 31

Figure 8:
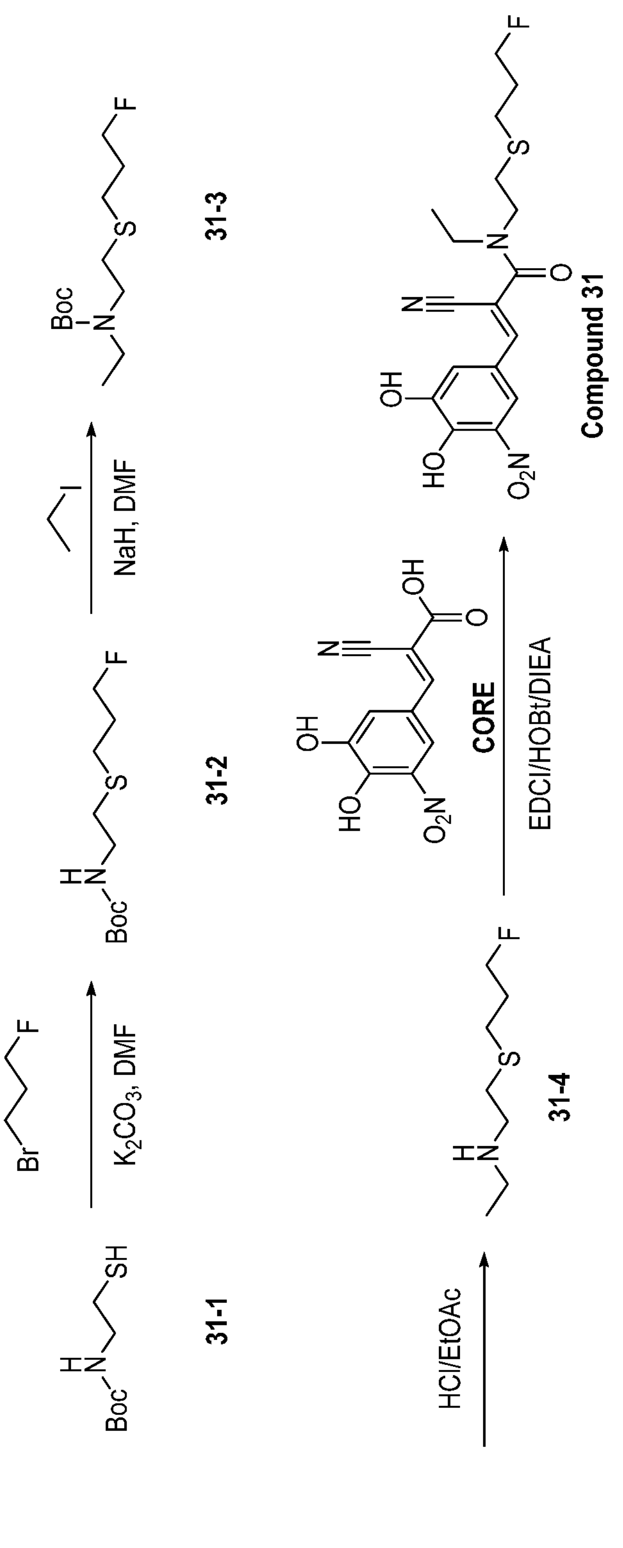
FIG. 8 shows synthetic schemes for Compound 31 described in Example 12.

Compound 31 is prepared according to the synthetic schemes shown in FIG. 8, and as described below.

Synthesis of compound 31-2: To a solution of compound 31-1 (3.54 g, 20.0 mmol) in DMF (50 mL) was added 1-bromo-3-fluoropropane (2.82 g, 20.0 mmol) and $K_2CO_3$ (5.53 g, 40.0 mmol) and the mixture was stirred at RT overnight. The mixture was concentrated under reduced pressure and the residue purified by silica gel chromatography (Pet.ether/EtOAc=10/1) to afford compound 31-2 (2.21 g, 47%) as a colorless oil. The compound was characterized by LC/MS and $^1$H NMR spectroscopies.

Synthesis of compound 31-3: To a solution of compound 31-2 (2.01 g, 8.50 mmol) in dry DMF (15 mL) at 0° C. was added NaH (60% suspension in oil, 1.02 g, 25.5 mmol) and the mixture was stirred at 0° C. for 30 min. Iodoethane (2.65 g, 17.0 mmol) was then added dropwise and the mixture was allowed to warm to RT and stirred for 2 h. The reaction was quenched with water and the mixture concentrated under reduced pressure. The residue was purified by silica gel chromatography (Petroleum ether/EtOAc=20/1) to afford compound 31-3 (1.28 g, 57%) as a colorless oil. The compound was characterized by LC/MS and $^1$H NMR spectroscopies.

Synthesis of compound 31-4: To a solution of compound 31-3 (280 mg, 1.05 mmol) in EtOAc (2 mL) was add a 4 M solution of HCl in EtOAc (2 mL) and the mixture was stirred for 1 h. The mixture was concentrated under reduced pressure to give compound 31-4 (165.3 mg, 78%) which was used directly in the next step.

Synthesis of compound 31: To a solution of compound 31-4 (165.3 mg, 0.822 mmol) and (E)-2-cyano-3-(3,4-dihydroxy-5-nitrophenyl) acrylic acid (250.2 mg, 1.00 mmol) in DMF (5 mL) was added HOBT (202.8 mg, 1.50 mmol), EDCI (287.6 mg, 1.5 mmol) and DIPEA (387.6 mg, 3.0 mmol) and the mixture was stirred at 30° C. for 16 h. The mixture was diluted with EtOAc, washed with water, brine, dried over $Na_2SO_4$ and concentrated under reduced pressure. The residue was purified by prep-HPLC (Agilent 10 prep-C18, 10 μm, 250×21.3 mm column, eluting with a gradient of ACN in water with 0.1% formic acid, at a flow rate of 20 mL/min) to give compound 4 (90 mg, 28%) as a yellow solid. The compound was characterized by LC/MS and $^1$H NMR spectroscopies.

Example 13: Synthetic Preparation of Compound 33

Figure 9:
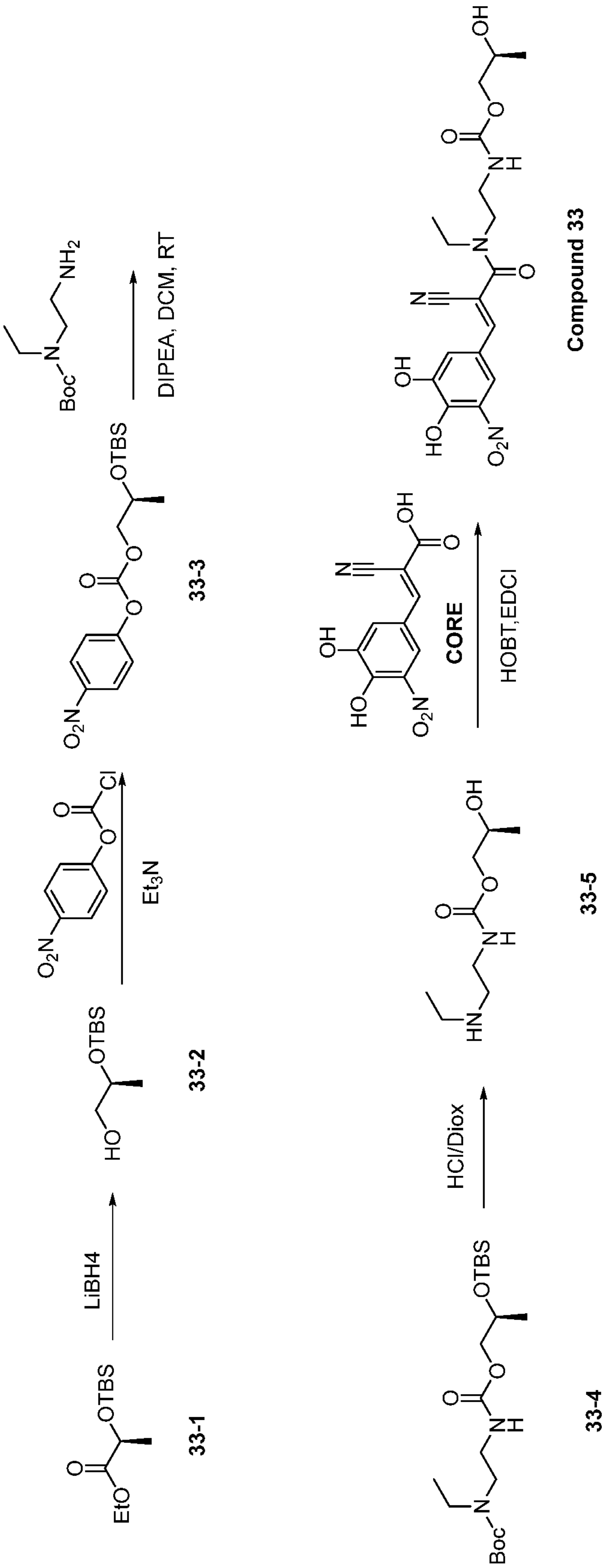
FIG. 9 shows synthetic schemes for Compound 33 described in Example 13.

Compound 33 is prepared according to the synthetic schemes shown in FIG. 9, and as described below.

Synthesis of 33-1: To a solution of compound 33-1 (10.0 g, 43.0 mmol) in $Et_2O$ (200 mL) at 0° C. was added MeOH (cat) and $LiBH_4$ (2 M solution in THF, 28.0 mL, 56.0 mmol). The mixture was stirred at 0° C. for 1.5 h, then allowed to warm to RT and stirred for a further 1.5 h. The reaction was quenched with water (150 mL) and the mixture extracted with EtOAc (100 mL×3). The combined organic layers were washed with water (150 mL×3), brine (50 mL), dried over $Na_2SO_4$ and concentrated under reduced pressure to afford compound 33-2 (7.0 g, 86%) as a colorless oil. The compound was characterized by LC/MS and $^1$H NMR spectroscopies.

Synthesis of 33-3: To a solution of 33-2 (3.5 g, 18.4 mmol) in DCM (30 mL) was added TEA (5.12 mL, 36.8 mmol) and 4-nitrophenyl carbonochloridate (4.45 g, 22.1 mmol) and the mixture was stirred at RT for 2 h. The mixture was diluted with water (50 mL), extracted with DCM (20 mL×3) and the combined organic layers washed with water (30 mL×3), brine (15 mL), dried over $Na_2SO_4$ and concentrated under reduced pressure. The residue was purified by silica gel chromatography (Pet.ether/EtOAc=10/1) to afford compound 33-3 (3.0 g, 46%) as a colorless oil. The compound was characterized by LC/MS and $^1$H NMR spectroscopies.

Synthesis of compound 33-4: To a solution of tert-butyl (2-aminoethyl) (ethyl) carbamate (528 mg, 2.81 mmol) and DIPEA (781 mg, 5.62 mmol) in DCM (10 mL) at 0° C. was added 33-3 (1 g, 2.81 mmol) and the mixture was stirred at RT for 2 h. The mixture was diluted with water (20 mL), extracted with DCM (10 mL×3) and the combined extracts washed with water (20 mL), brine (20 mL), dried over $Na_2SO_4$ and concentrated under reduced pressure. The residue was purified by silica gel chromatography (Pet.ether/EtOAc=2/1, v/v) to afford compound 33-4 (600 mg, 53%) as a colorless oil, which was used directly in the next step.

Synthesis of compound 33-5: To a solution of compound 33-4 (300 mg, 0.74 mmol) in DCM (5 mL) 0° C. was added a 4 M solution of HCl in dioxane (1 mL) and the mixture was stirred at RT for 20 h. The mixture was concentrated under reduced pressure to afford compound 33-5 (150 mg, 89%). The compound was used in the next step without purification.

Synthesis of compound 33: To a solution of (E)-2-cyano-3-(3,4-dihydroxy-5-nitrophenyl) acrylic acid (240 mg, 0.96 mmol) and DIPEA (435 mg, 3.36 mmol) in DMF (5 mL) at RT was added HOBT (260 mg, 1.92 mmol) and EDCI·HCl (276 mg, 1.44 mmol) and the mixture was stirred for 30 min. Compound 33-5 (200 mg, 0.88 mmol) was added and stirring was continued overnight. The mixture was diluted with water (20 mL), extracted with DCM (10 mL×3) and the combined organic layers were washed with water (20 mL), brine (20 mL), dried over $Na_2SO_4$ and concentrated under reduced pressure. The residue was purified by prep-HPLC (Agilent 10 prep-C18, 10 μm, 250×21.2 mm column, eluting with a gradient of MeOH in water with 0.1% formic acid, at a flow rate of 20 ml/min) to afford compound 13 (75 mg, 20%) as a red oil. The compound was characterized by LC/MS and $^1$H NMR spectroscopies.

Example 14: Synthetic Preparation of Compound 35

Figure 10:
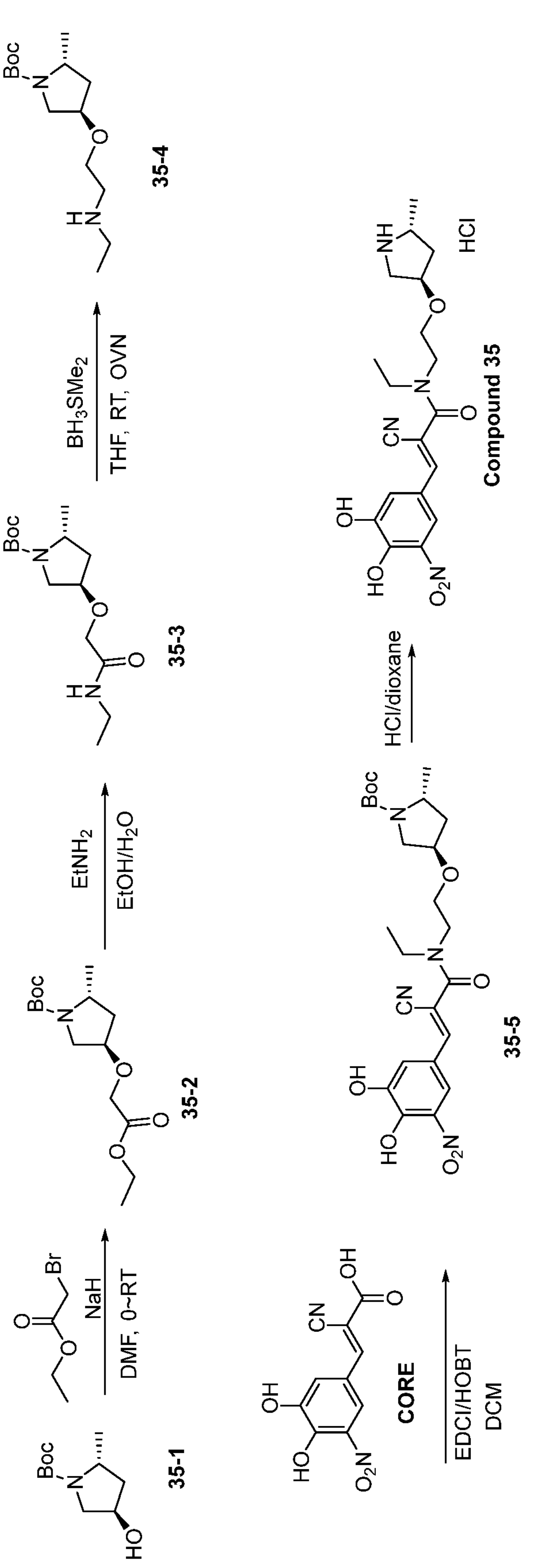
FIG. 10 shows synthetic schemes for Compound 35 described in Example 14.

Compound 35 is prepared according to the synthetic schemes shown in FIG. 10, and as described below.

Synthesis of 35-2: To a suspension of NaH (60% suspension in oil, 480 mg, 12.0 mmol) in DMF (20 mL) at 0° C. was added a solution of compound 35-1 (1.20 g, 6.0 mmol) in DMF (5 mL) and the mixture was stirred for 1 h. Ethyl 2-bromoacetate (1.50 g, 9.0 mmol) was added and the mixture was allowed to warm to RT and stirred for 16 h. The mixture was poured into cold water (100 mL), extracted with EtOAc (30 mL×3) and the combined organic layers were washed with water (100 ml×3), brine (100 mL), dried over $Na_2SO_4$ and concentrated under reduced pressure. The residue was purified by silica gel chromatography (Petroleum Ether/EtOAc=30/1, v/v) to afford compound 35-2 (900 mg, 52%) as a colorless oil. The compound was characterized by LC/MS and $^1$H NMR spectroscopies.

Synthesis of 35-3: A mixture of a 40% aqueous ethanamine solution (5.00 g) and compound 35-2 (900 mg, 3.13 mmol) in ethanol (5 mL) was heated at 80° C. in a 25 mL sealed tube for 16 h. The mixture was concentrated under reduced pressure and the residue purified by silica gel chromatography (EtOAc/Petroleum ether=1/5, v/v) to afford compound 35-3 (700 mg, 78%) as white solid. The compound was characterized by LC/MS and $^1$H NMR spectroscopies.

Synthesis of 35-4: To a solution of compound 35-3 (700 mg, 2.45 mmol) in dry THF (10 mL) at −20° C. was added Borane-methyl sulfide complex (1.0 mL, 10 mmol) via syringe slowly and the mixture was allowed to warm to RT and stirred overnight. The reaction was carefully quenched by addition of methanol (2 mL) and 1 M aqueous HCl (10 mL) and the mixture was stirred at RT for 20 h then concentrated under reduced pressure. The residue was diluted with a saturated aqueous $Na_2CO_3$ solution (10 mL), extracted with EtOAc (20 mL×5) and the combined organic layers were dried over $Na_2SO_4$ and concentrated under reduced pressure. The residue was purified by silica gel chromatography (DCM/MeOH=30/1, buffered with 0.5% $NH_3 \cdot H_2O$) to afford compound 35-4 (320 mg, 48%) as a colorless oil. The compound was characterized by LC/MS and $^1$H NMR spectroscopies.

Synthesis of compound 35-5: To a solution of (E)-2-cyano-3-(3,4-dihydroxy-5-nitrophenyl) acrylic acid (240 mg, 0.96 mmol) and DIPEA (435 mg, 3.36 mmol) in DCM (20 mL) at 0° C. was added HOBT (260 mg, 1.92 mmol) and EDCI·HCl (276 mg, 1.44 mmol) and the mixture was stirred for 30 min. A solution of compound 35-4 (260 mg, 0.95 mmol) in DCM (3 mL) was added and the mixture was allowed to warm to RT and stirred for 2 h. The mixture was diluted with water (20 mL), the layers were separated and the aqueous layer extracted with DCM (10 mL×3). The combined organic layers were washed with water (20 mL), brine (20 mL), dried over $Na_2SO_4$ and concentrated under reduced pressure. The residue was purified by silica gel chromatography (DCM/MeOH=50/1, v/v) followed by prep-TLC (DCM/MeOH=20/1, v/v) to afford compound 35-5 (150 mg, 31%) as red solid. The compound was characterized by LC/MS and $^1$H NMR spectroscopies.

Synthesis of compound 35: To a solution of compound 35-5 (170 mg, 0.34 mmol) in DCM (2 mL) at 0° C. was added a 4 M solution of HCl in dioxane (0.2 mL) and the mixture was stirred at RT for 20 h. The solvent was removed under reduced pressure and the residue purified by C18, RP column (Biotage, ACN/$H_2O$, 0-15%, buffered with 0.1% HCl) followed by prep-HPLC (Agilent 10 prep-C18, 10 μm, 250×21.2 mm column, eluting with a gradient of MeCN in water with 0.1% HCl, at a flow rate of 20 mL/min) to give compound 20 (17.6 mg, 12%) as a red solid. The compound was characterized by LC/MS and $^1$H NMR spectroscopies.

Example 15: Inhibition of RNA Demethylase Activity of FTO

An FTO activity assay was performed to determine the inhibitory activity of compounds provided herein towards FTO and compare them with entacapone. This assay measures the ability of FTO to demethylate an m6A methylated RNA substrate. The assay is specific to FTO and is not affected by the function of ALKBH5, which is another RNA demethylase in eukaryotic cells. This experiment showed that compound 1 and compound 31 show significantly higher FTO inhibitory activity compared to entacapone (see Table 4). For example, at 20 μM, entacapone exhibited less than 20% reduction of FTO activity whereas compound 1 and compound 31 exhibited about 40% or more of FTO activity inhibition. At twice the concentration, 40 μM, entacapone still exhibited less FTO activity inhibition than 20 UM compound 31.

TABLE 4

| | % FTO activity | | |
|---|---|---|---|
| | 0 μM | 20 μM | 40 μM |
| Entacapone | 100% | 83% | 61.5% |
| Compound 1 | 100% | 61% | 59% |
| Compound 31 | 100% | 54% | 48% |

Example 16: Determination of $IC_{50}$ for Compound 31 in Adult Glioblastoma

Glioma stem cells were incubated with various increasing concentrations of Compound 31 and the percentage of viable cells at 48 hours was quantified using Cell Titer Glo (Promega). This experiment showed an $IC_{50}$ of Compound 31 of 114.5 μM and an $IC_{10}$ of 70 μM. For the functional assays described below, the $IC_{10}$ was used to maintain at least 90% viability.

Example 17: Inhibition of Glioma Stem Cell Invasion by Compound 31

Figure 11:
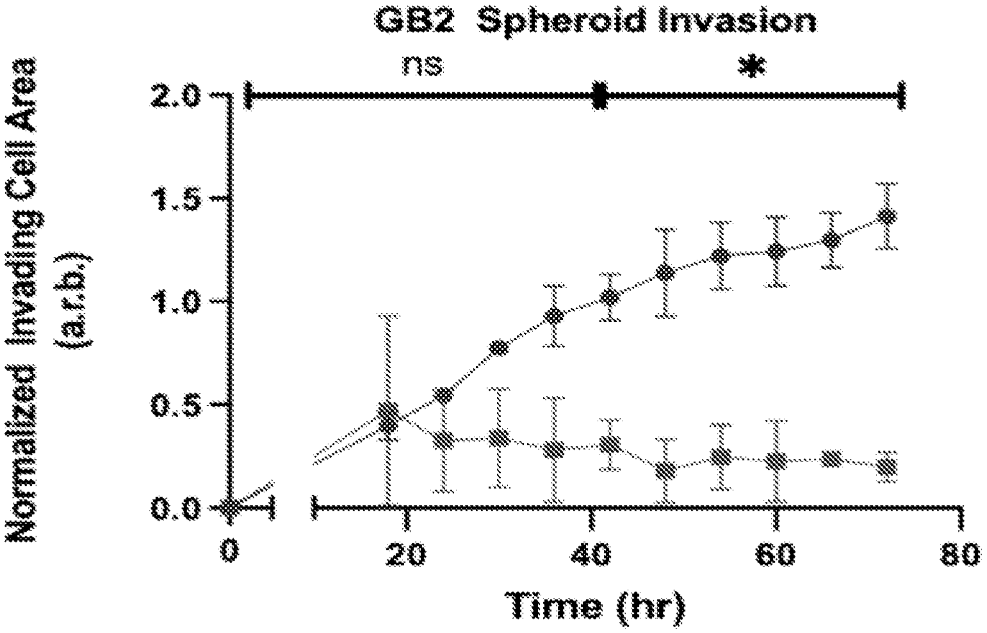
FIG. 11 shows the inhibition of glioma stem cell invasion by Compound 31 (squares) compared with control DMSO (circles).
Figure 12:
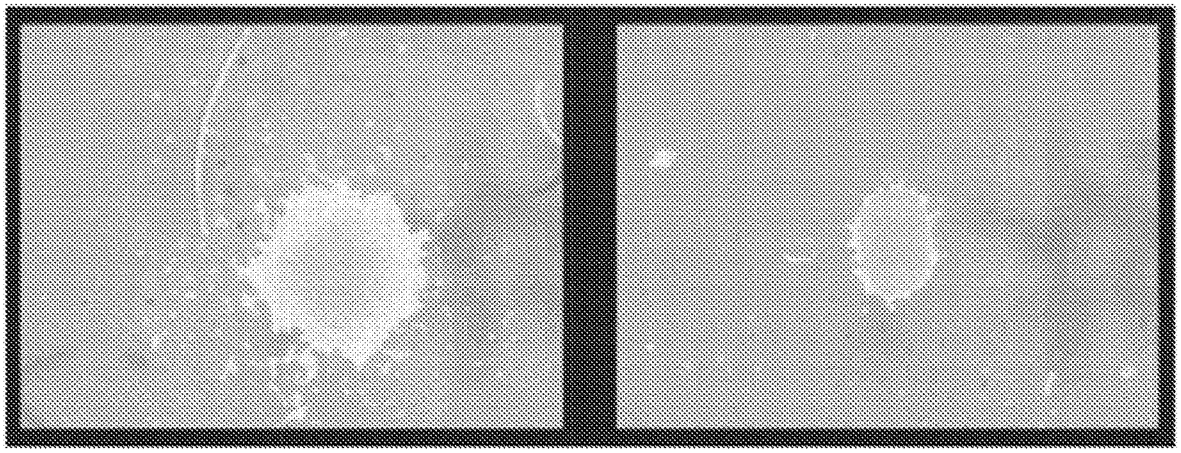
FIG. 12 shows the inhibition of glioma stem cell invasion by Compound 31 (right) compared with control DMSO (left).

Patient derived glioma stem cells (GSCs) were incubated with 70 μM Compound 31 or DMSO (control) for 72 hours and GSC invasion into the surrounding extracellular matrix was quantified in real time using Incucyte Cell Imager. As shown in FIG. 11 and FIG. 12, Compound 31 induces significant inhibition of GSC invasion ($p<0.05$). GSC invasion is one of the hallmarks of glioblastoma.

Example 18: Inhibition of Self-Renewal Ability of Pediatric DIPG Cells by Compound 31.

Figure 13:
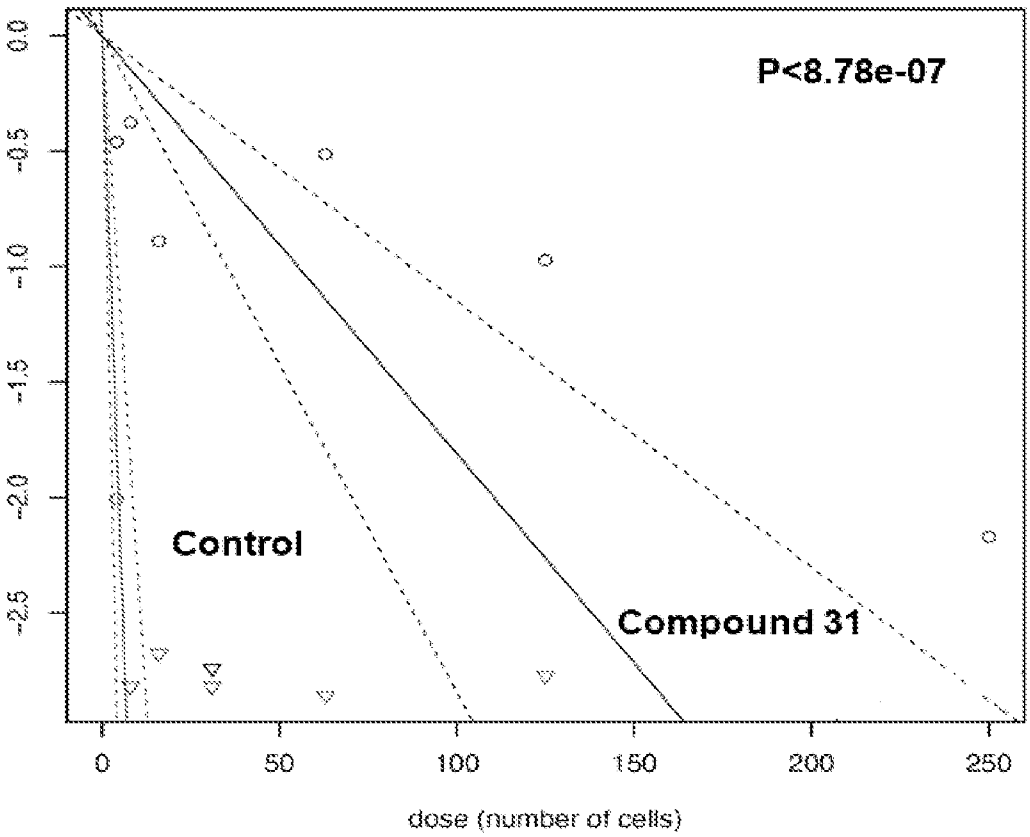
FIG. 13 shows Compound 31's inhibition of the self-renewal ability of diffuse intrinsic pontine glioma cells.

A limiting dilution assay (LDA) was used to determine the effect of FTO inhibition with Compound 31 on the self-renewal ability of diffuse intrinsic pontine glioma (DIPG) cells—a type of brain tumor found in an area of the brainstem known as the pons. With this assay DIPG cells are plated on 96-well plates in various numbers (2000 cell per well down to 1 cell per well) and the ability of cells to self-renew and form clonal tumor spheres is measured over a period of 2 weeks. The results, FIG. 13, showed that Compound 31 significantly inhibits the self-renewal ability of DIPG cells, which is a hallmark of this disease.

Example 19: Inhibition of Pediatric DIPG Cell Invasion by Compound 31

Figure 14:
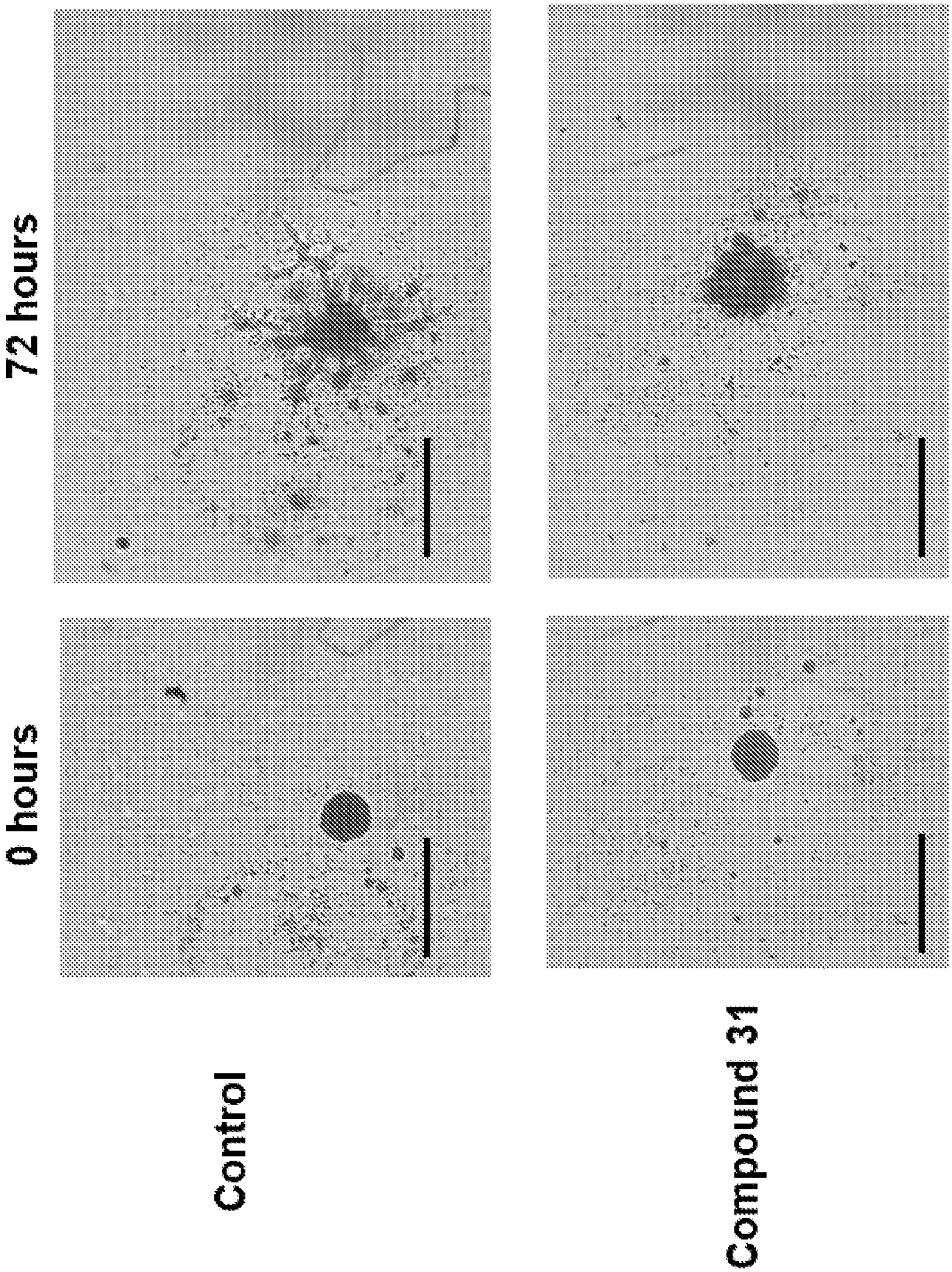
FIG. 14 shows the inhibition of diffuse intrinsic pontine glioma cell invasion by Compound 31 compared with control DMSO. The horizontal solid black bar represents 800 μm.
Figure 15:
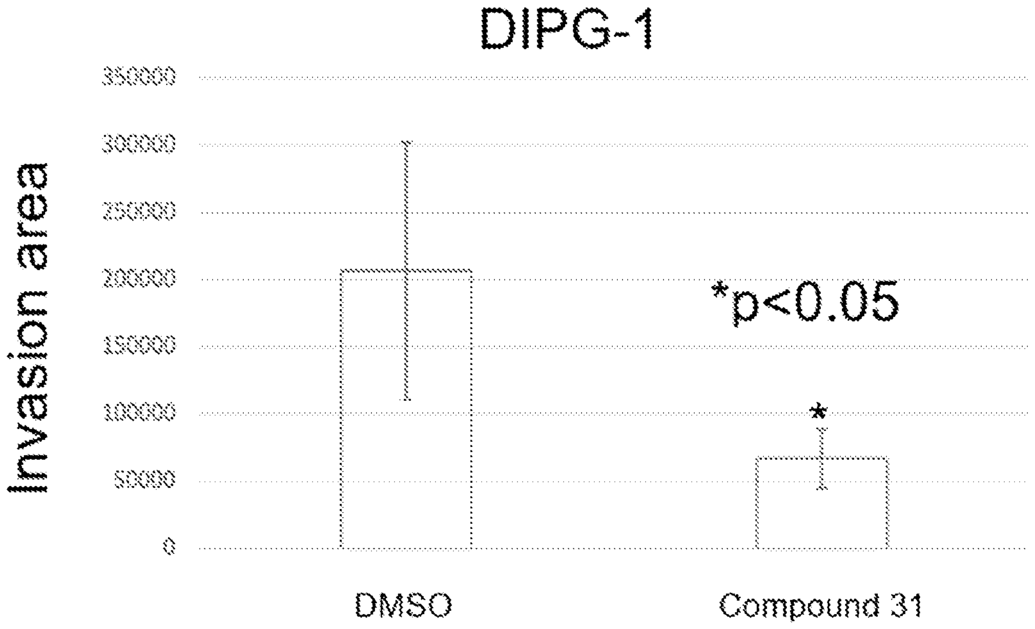
FIG. 15 shows the quantified inhibition of diffuse intrinsic pontine glioma cell invasion by Compound 31 compared with control DMSO.

Patient derived DIPG cells were incubated with 10 μM Compound 31 or DMSO (control) for 72 hours and DIPG invasion into the surrounding extracellular matrix was quantified in real time using Incucyte Cell Imager. As shown in FIG. 14 and FIG. 15, Compound 31 induces significant inhibition of DIPG invasion ($p<0.05$).

It is to be understood that wherever values and ranges are provided herein, all values and ranges encompassed by these values and ranges, or a combination of these values and ranges, are meant to be encompassed within the scope of the aspects and embodiments provided herein. Moreover, all values that fall within these ranges, as well as the upper or lower limits of a range of values, are also contemplated by the present application.

Unless otherwise defined, all technical and scientific terms used herein are accorded the meaning commonly known to one of ordinary skill in the art.

Those skilled in the art will recognize, or be able to ascertain using no more than routine experimentation, many equivalents of the specific embodiments provided herein. Such equivalents are intended to be encompassed by the following claims.

The invention claimed is:

1. A compound, having the following formula:

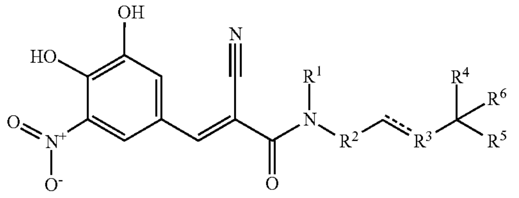

or a pharmaceutically acceptable salt thereof, wherein

 is a single or double bond;

$R^1$ is $C_{1-4}$ alkyl;

$R^2$ is $C_{1-4}$ alkylene;

$R^3$ is N, O, S, NH, CH, or N—($C_{1-4}$ alkyl);

$R^4$ is H, $C_{1-4}$ alkyl, or ($C_{1-4}$ alkyl)-OH;

or $R^3$ and $R^4$ combine to form a $C_{2-6}$ heterocycloalkyl;

$R^5$ is C(O)N(H)($C_{1-4}$ alkyl), C(O)N(H)($C_{2-6}$ heterocycloalkyl), heteroaryl, heteroaryl-($C_{1-4}$ alkyl), C(O)H, CN, pyrrolidinonyl, $C_{1-4}$ alkyl, $C_{1-4}$ haloalkyl, C(O)O($C_{1-4}$ alkyl), C(O)$NH_2$, C(O)N(H)C(O)H, ($C_{1-4}$ alkyl)-OH, $C_{2-6}$ heterocycloalkyl-C(O)H, or O—($C_{1-4}$ alkyl);

or $R^4$ and $R^5$ combine to form CO, $C_{3-7}$ cycloalkyl, $C_{2-6}$ heterocycloalkyl, pyrrolidinonyl, pyrrolidinonyl-($C_{1-4}$ alkyl), or imidazolidinonyl-OH; and $R^6$ is H, CN, C(O)H, $C_{1-4}$ alkyl, heteroaryl, O—($C_{1-4}$ alkyl), O—($C_{1-4}$ alkyl)-OH, N(H)—($C_{1-4}$ alkyl), or N(H)—($C_{1-4}$ alkyl)-OH.

2. The compound of claim 1, wherein $R^1$ is methyl or ethyl.

3. The compound of claim 1, wherein $R^2$ is methylene.

4. The compound of claim 1, wherein  is a single bond, and $R^3$ is N, O, or S.

5. The compound of claim 1, wherein  is a double bond, and $R^3$ is NH or CH.

6. The compound of claim 1, wherein $R^4$ is H or $C_{1-4}$ alkyl.

7. The compound of claim 1, wherein each instance of heteroaryl refers, independently, to furanyl, pyridinyl, pyrimidinyl, pyrazinyl, triazinyl, pyrrolyl, pyrazolyl, or imidazolyl.

8. The compound of claim 1, wherein $R^3$ and $R^4$ combine to form a $C_{2-6}$ heterocycloalkyl.

9. The compound of claim 1, wherein $R^4$ and $R^5$ combine to form CO, $C_{3-7}$ cycloalkyl, pyrrolidinonyl, pyrrolidinonyl-($C_{1-4}$ alkyl), or imidazolidinonyl-OH.

10. The compound of claim 1, wherein:

$R^3$ is N, O, S, NH, CH, or N—($C_{1-4}$ alkyl);

$R^4$ is H, $C_{1-4}$ alkyl, or ($C_{1-4}$ alkyl)-OH; and $R^5$ is C(O)N(H)($C_{1-4}$ alkyl), heteroaryl, heteroaryl-($C_{1-4}$ alkyl), C(O)H, CN, pyrrolidinonyl, $C_{1-4}$ alkyl, $C_{1-4}$ haloalkyl, C(O)O($C_{1-4}$ alkyl), C(O)$NH_2$, C(O)N(H)C(O)H, ($C_{1-4}$ alkyl)-OH, or O—($C_{1-4}$ alkyl).

11. The compound of claim 1, having the formula:
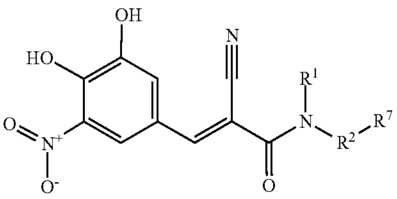
or a pharmaceutically acceptable salt thereof, wherein
$R^7$ is
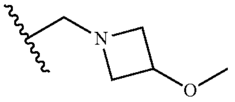,
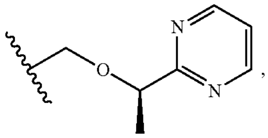,
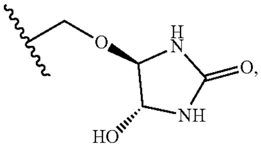
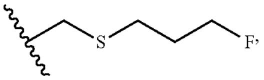
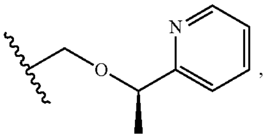,
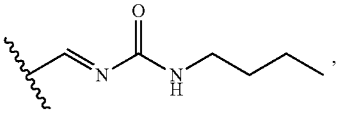,
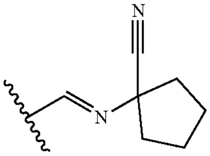,
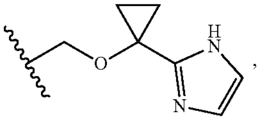,
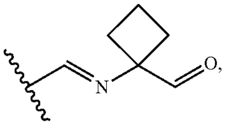
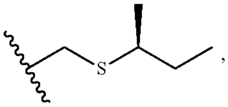,
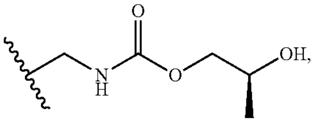
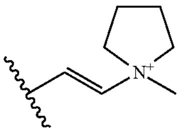,
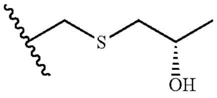,
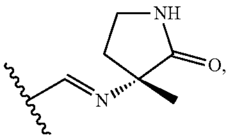
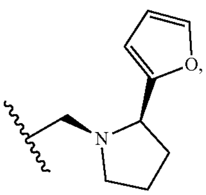
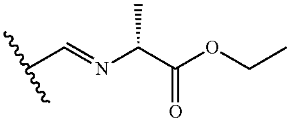,
-continued
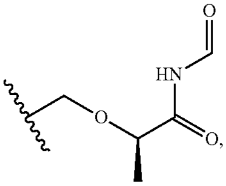
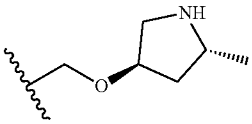,
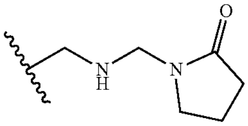,
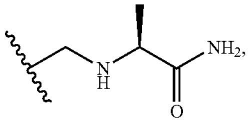
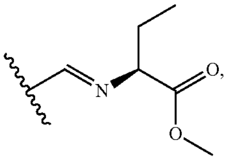
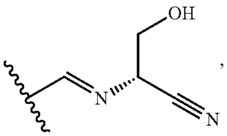,
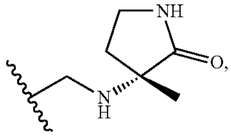
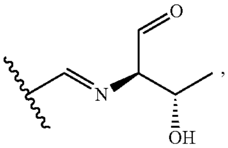,
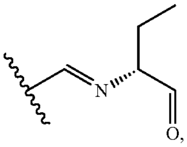
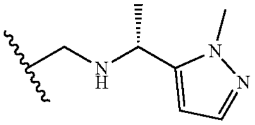,
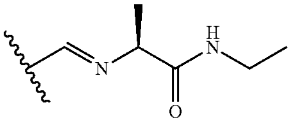,
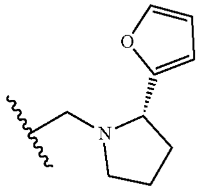,
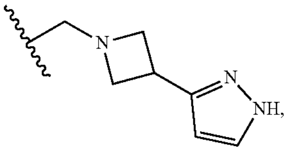
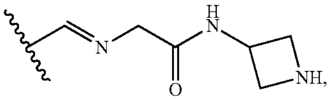
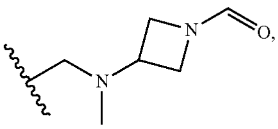
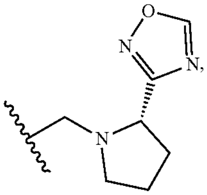 or
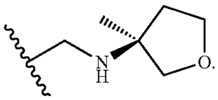 [SMILES: *CN[C@@]1(C)CCOC1]

12. The compound of claim 1, wherein the compound is selected from:
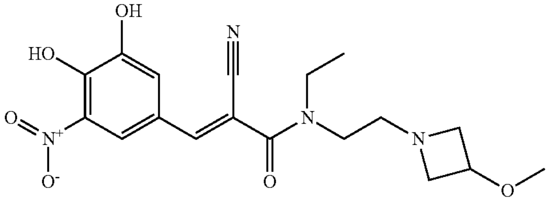
,
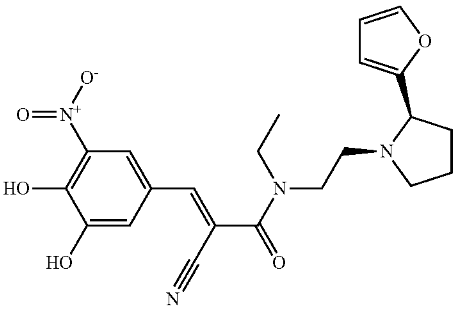
,
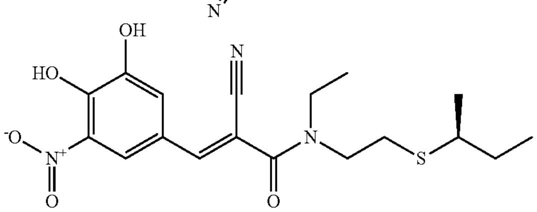
,
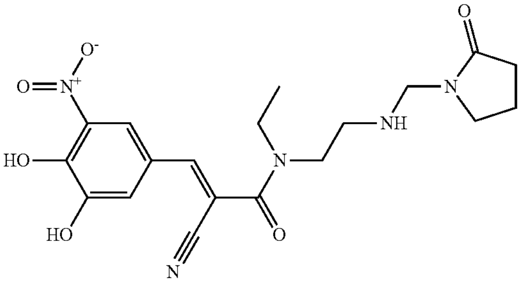
,
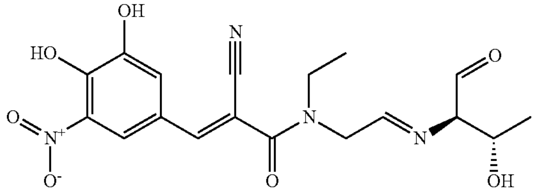
,
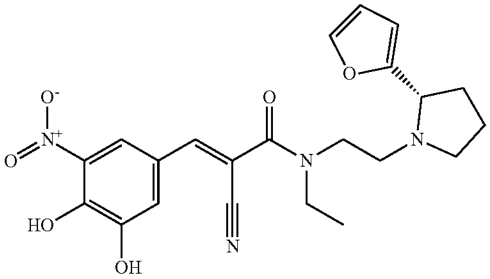
,
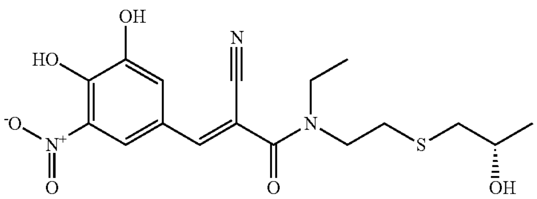
,
-continued
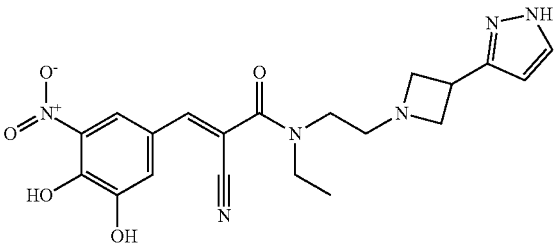
,
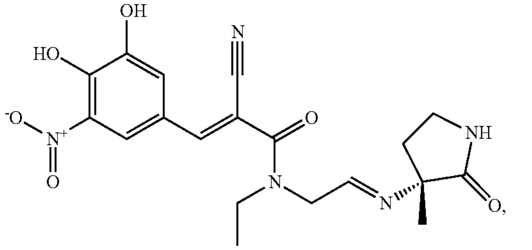
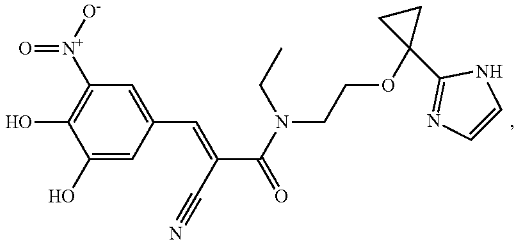
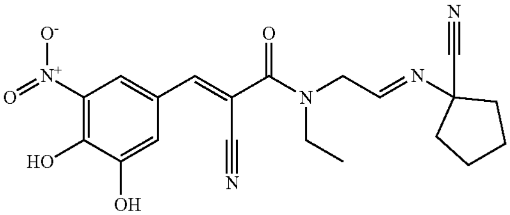
,
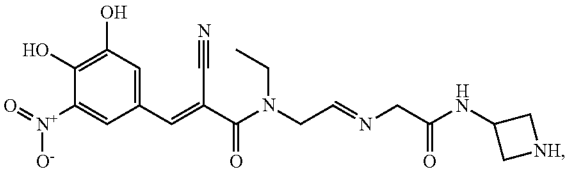
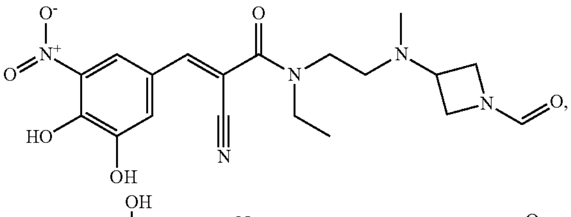
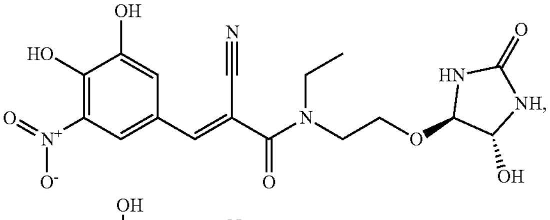
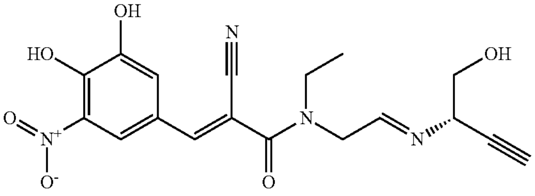
, -continued
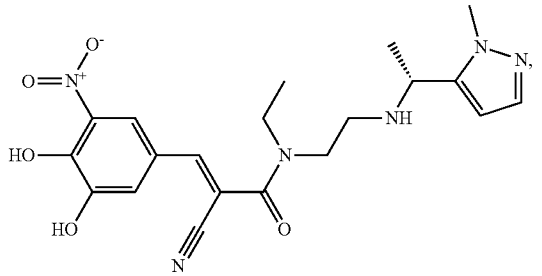
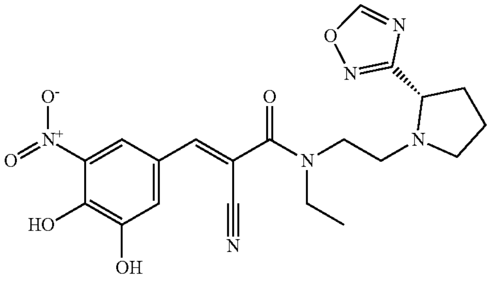
,
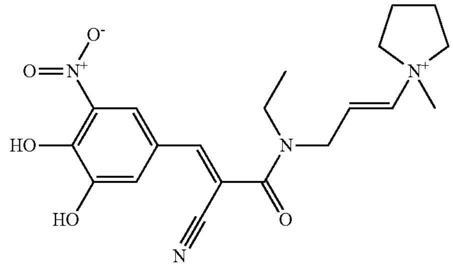
,
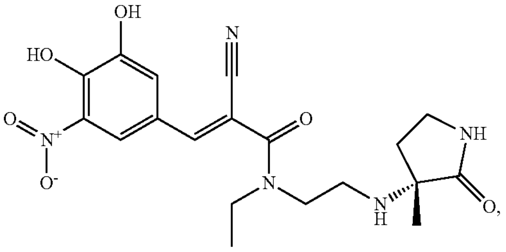
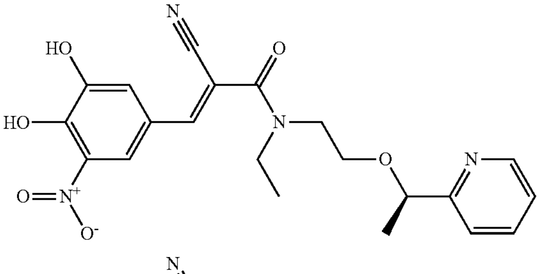
,
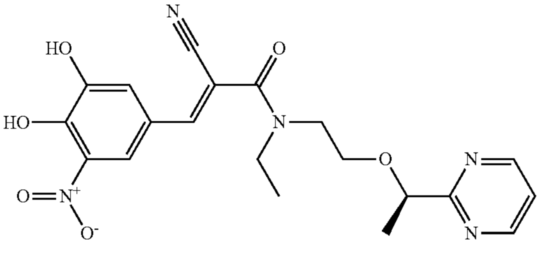
,
-continued
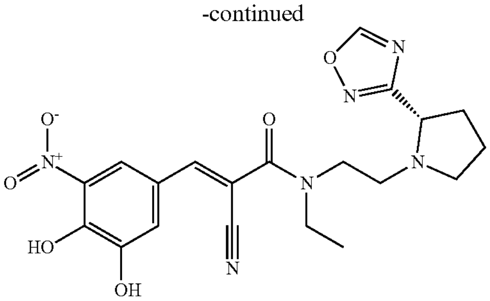
,
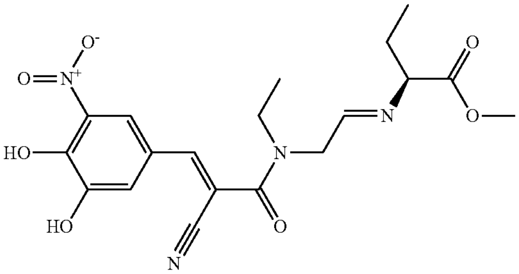
,
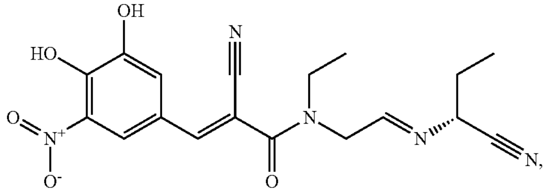
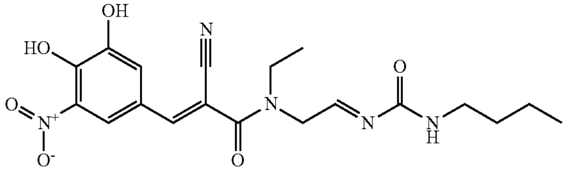
,
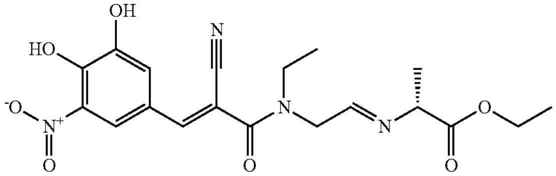
,
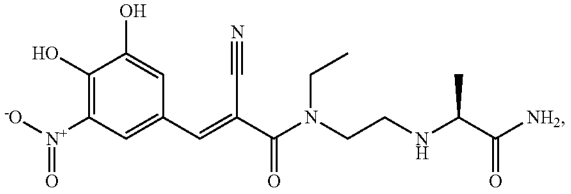
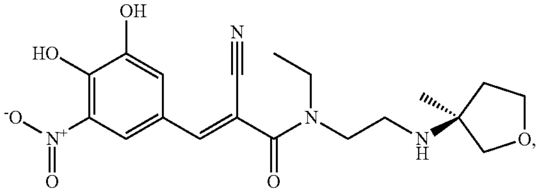
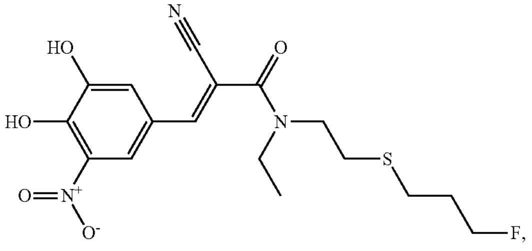

-continued

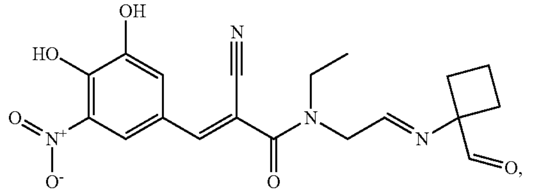

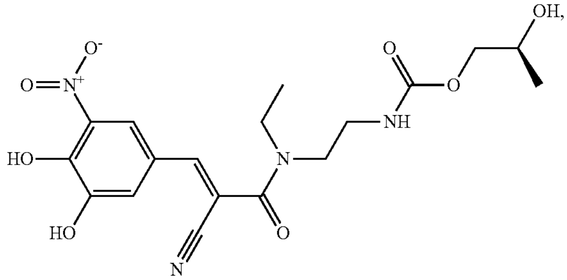

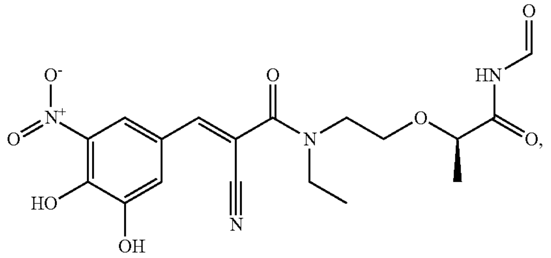

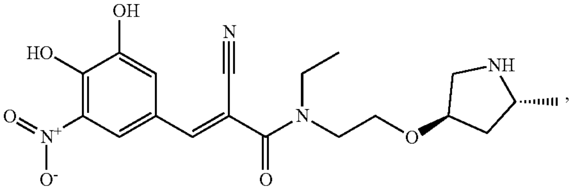

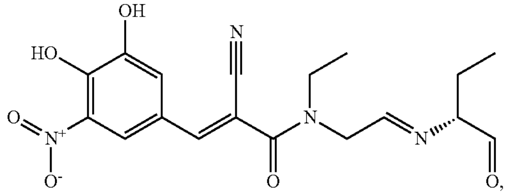

or

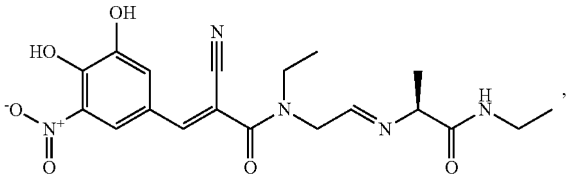

or a pharmaceutically acceptable salt thereof.

13. A composition, comprising the compound of claim 1.

14. The composition of claim 13, wherein the composition is a pharmaceutical composition further comprising a pharmaceutical acceptable carrier.

15. A method of treating a cancer in a subject in need thereof, comprising administering a therapeutically effective amount of a compound, having the following formula:

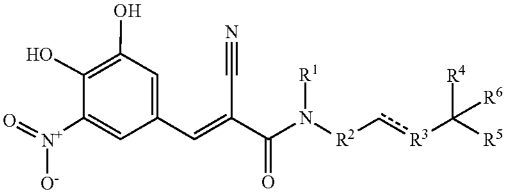

or a pharmaceutically acceptable salt thereof, wherein

 is a single or double bond;

$R^1$ is $C_{1-4}$ alkyl;

$R^2$ is $C_{1-4}$ alkylene;

$R^3$ is N, O, S, NH, CH, or N—($C_{1-4}$ alkyl);

$R^4$ is H, $C_{1-4}$ alkyl, or ($C_{1-4}$ alkyl)-OH;

or $R^3$ and $R^4$ combine to form a $C_{2-6}$ heterocycloalkyl;

$R^5$ is C(O)N(H) ($C_{1-4}$ alkyl), C(O)N(H)($C_{2-6}$ heterocycloalkyl), heteroaryl, heteroaryl-($C_{1-4}$ alkyl), C(O)H, CN, pyrrolidinonyl, $C_{1-4}$ alkyl, $C_{1-4}$ haloalkyl, C(O)O ($C_{1-4}$ alkyl), C(O)$NH_2$, C(O)N(H)C(O)H, ($C_{1-4}$ alkyl)-OH, $C_{2-6}$ heterocycloalkyl-C(O)H, or O—($C_{1-4}$ alkyl);

or $R^4$ and $R^5$ combine to form CO, $C_{3-7}$ cycloalkyl, $C_{2-6}$ heterocycloalkyl, pyrrolidinonyl, pyrrolidinonyl-($C_{1-4}$ alkyl), or imidazolidinonyl-OH; and $R^6$ is H, CN, C(O)H, $C_{1-4}$ alkyl, heteroaryl, O—($C_{1-4}$ alkyl), O—($C_{1-4}$ alkyl)-OH, N(H)—($C_{1-4}$ alkyl), or N(H)—($C_{1-4}$ alkyl)-OH.

16. The method of claim 15, wherein the cancer comprises a brain tumor.

17. The method of claim 15, wherein the cancer comprises a glioblastoma or a diffuse intrinsic pontine glioma.

18. The method of claim 15, wherein the cancer comprises a brain cancer or tumor, a leukemia, a breast cancer, a lung cancer, a colon cancer, a pancreatic cancer, an ovarian cancer, a prostate cancer, or a kidney cancer.

19. A method of inhibiting fat mass obesity-associated protein (FTO) or Notch1 activity in a cell, comprising contacting the cell with an effective amount of a compound, having the following formula:

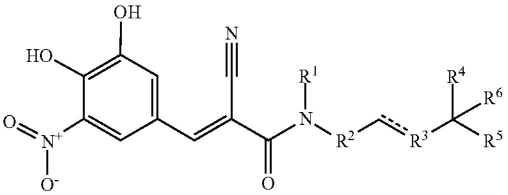

or a pharmaceutically acceptable salt thereof, wherein

 is a single or double bond;

$R^1$ is $C_{1-4}$ alkyl;

$R^2$ is $C_{1-4}$ alkylene;

$R^3$ is N, O, S, NH, CH, or N—($C_{1-4}$ alkyl);

$R^4$ is H, $C_{1-4}$ alkyl, or ($C_{1-4}$ alkyl)-OH;

or $R^3$ and $R^4$ combine to form a $C_{2-6}$ heterocycloalkyl;

$R^5$ is C(O)N(H)($C_{1-4}$ alkyl), C(O)N(H)($C_{2-6}$ heterocycloalkyl), heteroaryl, heteroaryl-($C_{1-4}$ alkyl), C(O)H, CN, pyrrolidinonyl, $C_{1-4}$ alkyl, $C_{1-4}$ haloalkyl, C(O)O ($C_{1-4}$ alkyl), C(O)$NH_2$, C(O)N(H)C(O)H, ($C_{1-4}$ alkyl)-OH, $C_{2-6}$ heterocycloalkyl-C(O)H, or O—($C_{1-4}$ alkyl);

or $R^4$ and $R^5$ combine to form CO, $C_{3-7}$ cycloalkyl, $C_{2-6}$ heterocycloalkyl, pyrrolidinonyl, pyrrolidinonyl-($C_{1-4}$ alkyl), or imidazolidinonyl-OH; and $R^6$ is H, CN, C(O)H, $C_{1-4}$ alkyl, heteroaryl, O—($C_{1-4}$ alkyl), O—($C_{1-4}$ alkyl)-OH, N(H)—($C_{1-4}$ alkyl), or N(H)—($C_{1-4}$ alkyl)-OH.

20. The method of claim 19, wherein:

the cell is a brain cell, a blood cell, a breast cell, a lung cell, a colon cell, a pancreatic cell, an ovarian cell, a prostate cell, or a kidney cell, and optionally the contacting is in a subject; or the contacting is in vitro, and optionally the cell is a brain cell, a blood cell, a breast cell, a lung cell, a colon cell, a pancreatic cell, an ovarian cell, a prostate cell, or a kidney cell.

21. The method of claim 19, wherein the cell is a glioma stem cell.

* * * * *